(12) United States Patent
Okazaki et al.

(10) Patent No.: US 8,808,173 B2
(45) Date of Patent: Aug. 19, 2014

(54) SPACE ENSURING DEVICE

(75) Inventors: Yoshiro Okazaki, Tokyo (JP);
Michihiro Sugahara, Tokyo (JP);
Mamoru Kaneko, Saitama (JP)

(73) Assignee: Olympus Corporation, Tokyo (JP)

( * ) Notice: Subject to any disclaimer, the term of this patent is extended or adjusted under 35 U.S.C. 154(b) by 464 days.

(21) Appl. No.: 12/884,629

(22) Filed: Sep. 17, 2010

(65) Prior Publication Data
US 2011/0071342 A1    Mar. 24, 2011

Related U.S. Application Data

(60) Provisional application No. 61/244,586, filed on Sep. 22, 2009.

(30) Foreign Application Priority Data

May 25, 2010   (JP) .................................. 2010-119749

(51) Int. Cl.
*A61B 1/32* (2006.01)
*A61B 17/34* (2006.01)

(52) U.S. Cl.
CPC ..... *A61B 17/3431* (2013.01); *A61B 2017/3449* (2013.01)
USPC ............ 600/206; 600/201; 600/235; 600/246

(58) Field of Classification Search
CPC ........... A61B 17/3431; A61B 17/3423; A61B 17/3462; A61B 17/3466; A61B 2017/3449
USPC ......... 600/201, 204–207, 212, 214, 219, 245, 600/246, 237–244; 606/248–249
See application file for complete search history.

(56) References Cited

U.S. PATENT DOCUMENTS 3,281,141 A    10/1966 Smiley et al.
3,859,985 A     1/1975 Eckhart
(Continued)

FOREIGN PATENT DOCUMENTS

FR    2 914 840    10/2008
JP    62-035318     2/1987
(Continued)

OTHER PUBLICATIONS

Sosa et al., "A New Technique to Perform Epicardial Mapping in the Electrophysiology Laboratory", Journal of Cardiovascular Electrophysiology, Apr. 29, 2007, pp. 531-536, vol. 7, Issue 6.

(Continued)

*Primary Examiner* — Ellen C Hammond
*Assistant Examiner* — Stuart S Bray
(74) *Attorney, Agent, or Firm* — Scully, Scott, Murphy & Presser, P.C.

(57) ABSTRACT

In a pericardioscopic procedure, without providing an endoscope or surgical instrument with special space ensuring means and without unnecessarily dilating the pericardial space, a space necessary for operation of the endoscope or surgical instrument is ensured, so that maneuverability is improved while suppressing complications. Provided is a space ensuring device comprising: a pericardium pressing part for pressing a pericardium from the pericardial space side; a heart pressing part for pressing the surface of a heart from the pericardial space side; and an interconnecting part interconnecting the pericardium pressing part and the heart pressing part, wherein the interconnecting part generates the resilient force enabling expansion against a pressure applied by a pericardium and a heart so as to ensure a space between the pericardium pressing part and the heart pressing part.

6 Claims, 16 Drawing Sheets

(56) References Cited

U.S. PATENT DOCUMENTS

| | | | |
|---|---|---|---|
| 4,063,553 A | 12/1977 | Karsh | |
| 4,224,929 A | 9/1980 | Furihata | |
| 4,319,568 A | 3/1982 | Tregoning | |
| 4,829,448 A | 5/1989 | Balding et al. | |
| 4,884,567 A | 12/1989 | Elliott et al. | |
| 4,991,603 A | 2/1991 | Cohen et al. | |
| 5,035,231 A | 7/1991 | Kubokawa et al. | |
| 5,048,537 A | 9/1991 | Messinger | |
| 5,297,536 A | 3/1994 | Wilk | |
| 5,309,896 A | 5/1994 | Moll et al. | |
| 5,324,266 A | 6/1994 | Ambrisco et al. | |
| 5,336,252 A | 8/1994 | Cohen | |
| 5,400,773 A | 3/1995 | Zhu et al. | |
| 5,549,569 A | 8/1996 | Lynn et al. | |
| 5,697,916 A | 12/1997 | Schraga | |
| 5,725,525 A | 3/1998 | Kordis | |
| 5,735,791 A * | 4/1998 | Alexander et al. | 600/37 |
| 5,759,150 A * | 6/1998 | Konou et al. | 600/114 |
| 5,968,017 A | 10/1999 | Lampropoulos et al. | |
| 6,015,382 A * | 1/2000 | Zwart et al. | 600/207 |
| 6,017,332 A | 1/2000 | Urrutia | |
| 6,071,295 A * | 6/2000 | Takahashi | 606/191 |
| 6,203,490 B1 * | 3/2001 | Krajicek | 600/37 |
| 6,251,093 B1 | 6/2001 | Valley et al. | |
| 6,267,717 B1 | 7/2001 | Stoll et al. | |
| 6,338,710 B1 * | 1/2002 | Takahashi et al. | 600/37 |
| 6,371,910 B1 * | 4/2002 | Zwart et al. | 600/207 |
| 6,390,976 B1 * | 5/2002 | Spence et al. | 600/210 |
| 6,471,644 B1 * | 10/2002 | Sidor, Jr. | 600/204 |
| 6,478,029 B1 * | 11/2002 | Boyd et al. | 128/898 |
| 6,699,259 B2 * | 3/2004 | Fogarty et al. | 606/192 |
| 6,701,930 B2 * | 3/2004 | Benetti et al. | 128/898 |
| 6,705,988 B2 * | 3/2004 | Spence et al. | 600/201 |
| 6,706,013 B1 | 3/2004 | Bhat et al. | |
| 6,740,082 B2 * | 5/2004 | Shadduck | 606/41 |
| 6,743,169 B1 * | 6/2004 | Taylor et al. | 600/204 |
| 6,890,295 B2 * | 5/2005 | Michels et al. | 600/114 |
| 7,022,118 B2 | 4/2006 | Ariura et al. | |
| 7,229,408 B2 * | 6/2007 | Douglas et al. | 600/214 |
| 7,394,976 B2 | 7/2008 | Entenman et al. | |
| 7,398,781 B1 | 7/2008 | Chin | |
| 7,399,272 B2 * | 7/2008 | Kim et al. | 600/37 |
| 7,485,624 B2 | 2/2009 | Donovan | |
| 7,621,867 B2 | 11/2009 | Kura et al. | |
| 7,914,444 B2 | 3/2011 | Moriyama et al. | |
| 8,002,802 B2 * | 8/2011 | Abdou | 606/248 |
| 8,109,903 B2 | 2/2012 | Terliuc et al. | |
| 8,246,539 B2 * | 8/2012 | Hjelle et al. | 600/208 |
| 8,409,078 B2 | 4/2013 | Ikeda | |
| 8,480,569 B2 | 7/2013 | Terliuc et al. | |
| 2002/0010388 A1 * | 1/2002 | Taylor et al. | 600/204 |
| 2002/0099270 A1 * | 7/2002 | Taylor et al. | 600/204 |
| 2004/0064138 A1 | 4/2004 | Grabek | |
| 2004/0153098 A1 | 8/2004 | Chin et al. | |
| 2004/0230099 A1 * | 11/2004 | Taylor et al. | 600/204 |
| 2005/0049463 A1 * | 3/2005 | Arai et al. | 600/210 |
| 2005/0065409 A1 * | 3/2005 | de la Torre et al. | 600/204 |
| 2005/0159645 A1 * | 7/2005 | Bertolero et al. | 600/116 |
| 2005/0209506 A1 | 9/2005 | Butler et al. | |
| 2006/0155169 A1 | 7/2006 | Bastia et al. | |
| 2006/0200002 A1 * | 9/2006 | Guenst | 600/201 |
| 2006/0259017 A1 * | 11/2006 | Heil et al. | 606/1 |
| 2006/0287577 A1 * | 12/2006 | Wendlandt | 600/146 |
| 2006/0293662 A1 * | 12/2006 | Boyer et al. | 606/61 |
| 2007/0023334 A1 | 2/2007 | Hallstadius et al. | |
| 2007/0088203 A1 * | 4/2007 | Lau | 600/205 |
| 2007/0135686 A1 * | 6/2007 | Pruitt et al. | 600/214 |
| 2007/0255100 A1 * | 11/2007 | Barlow et al. | 600/114 |
| 2008/0015569 A1 | 1/2008 | Saadat et al. | |
| 2008/0033467 A1 | 2/2008 | Miyamoto et al. | |
| 2008/0096165 A1 * | 4/2008 | Virnicchi et al. | 433/140 |
| 2008/0132954 A1 * | 6/2008 | Sekhon et al. | 606/280 |
| 2008/0167621 A1 | 7/2008 | Wagner et al. | |
| 2008/0275371 A1 | 11/2008 | Hoffmann | |
| 2009/0043166 A1 | 2/2009 | Ishii | |
| 2009/0054943 A1 | 2/2009 | Qu et al. | |
| 2009/0171152 A1 | 7/2009 | Aoki et al. | |
| 2009/0299364 A1 | 12/2009 | Batchelor et al. | |
| 2009/0318759 A1 * | 12/2009 | Jacobsen et al. | 600/116 |
| 2010/0041949 A1 | 2/2010 | Tolkowsky | |
| 2010/0145361 A1 | 6/2010 | Francischelli et al. | |
| 2010/0191164 A1 | 7/2010 | Sasaki et al. | |
| 2010/0268029 A1 * | 10/2010 | Phan et al. | 600/115 |
| 2010/0317925 A1 | 12/2010 | Banchieri et al. | |
| 2011/0082452 A1 | 4/2011 | Melsky et al. | |
| 2011/0144572 A1 | 6/2011 | Kassab et al. | |
| 2012/0277538 A1 * | 11/2012 | Okada | 600/204 |
| 2012/0277796 A1 * | 11/2012 | Gabelberger et al. | 606/249 |
| 2012/0283766 A1 | 11/2012 | Makower et al. | |
| 2013/0012782 A1 * | 1/2013 | Stearns et al. | 600/202 |

FOREIGN PATENT DOCUMENTS

| | | |
|---|---|---|
| JP | 64-20836 | 1/1989 |
| JP | 2-55960 | 4/1990 |
| JP | 6507810 A | 9/1994 |
| JP | 7501959 A | 3/1995 |
| JP | 07-265321 | 10/1995 |
| JP | 08-117232 | 5/1996 |
| JP | 08-280815 | 10/1996 |
| JP | 975353 A | 3/1997 |
| JP | 09-187415 | 7/1997 |
| JP | 10234738 A | 9/1998 |
| JP | 11-276422 | 10/1999 |
| JP | 200023988 A | 1/2000 |
| JP | 2000-176011 | 6/2000 |
| JP | 2001-519212 | 10/2001 |
| JP | 2001-340462 | 12/2001 |
| JP | 2002-017854 | 1/2002 |
| JP | 2002-522116 | 7/2002 |
| JP | 2003-144378 | 5/2003 |
| JP | 2003529390 A | 10/2003 |
| JP | 2004-033525 | 2/2004 |
| JP | 2004-081852 | 3/2004 |
| JP | 2004-097391 | 4/2004 |
| JP | 2004-105226 | 4/2004 |
| JP | 2006-271831 | 10/2006 |
| JP | 2007-054333 | 3/2007 |
| JP | 2007-505680 | 3/2007 |
| JP | 3143693 | 7/2008 |
| JP | 2008-540117 | 11/2008 |
| WO | 9221295 A1 | 12/1992 |
| WO | 9309722 A1 | 5/1993 |
| WO | WO 93/09722 | 5/1993 |
| WO | WO 96/40368 | 12/1996 |
| WO | WO 97/10753 | 3/1997 |
| WO | WO 98/24378 | 6/1998 |
| WO | 9837814 A1 | 9/1998 |
| WO | WO 99/13936 | 3/1999 |
| WO | WO 99/60924 | 12/1999 |
| WO | WO 00/07530 | 2/2000 |
| WO | 0062680 A1 | 10/2000 |
| WO | WO 01/78809 A1 | 10/2001 |
| WO | WO 2004/012586 A2 | 2/2004 |
| WO | WO 2006/058434 A1 | 6/2006 |
| WO | 2008140117 A1 | 11/2008 |
| WO | WO 2008/134457 A1 | 11/2008 |
| WO | WO 2009/004777 A1 | 1/2009 |

OTHER PUBLICATIONS

Abstract only of WO 2005/028001.
Abstract only of WO 2006/124634.
Abstract of WO 99/19008 A1.
International Search Report dated Oct. 19, 2010.
International Search Report dated Oct. 26, 2010.
International Search Report dated Dec. 7, 2010 together with an English language abstract.
U.S. Office Action dated Aug. 16, 2012 issued in U.S. related U.S. Appl. No. 12/884,845.
U.S. Office Action dated Aug. 27, 2012 issued in U.S. related U.S. Appl. No. 12/757,210.
U.S. Office Action dated Aug. 31, 2012 issued in U.S. related U.S. Appl. No. 12/871,172.

(56) References Cited

OTHER PUBLICATIONS

U.S. Final Office Action dated Sep. 4, 2013 issued in corresponding U.S. Appl. No. 12/714,827.
U.S. Final Office Action dated Oct. 1, 2013 issued in corresponding U.S. Appl. No. 12/757,210.
U.S. Final Office Action dated Jan. 18, 2013 issued in corresponding U.S. Appl. No. 12/871,172.
U.S. Final Office Action dated Feb. 4, 2013 issued in corresponding U.S. Appl. No. 12/757,210.
U.S. Final Office Action dated Feb. 7, 2013 issued in corresponding U.S. Appl. No. 12/884,845.
U.S. Non-Final Office Action dated Feb. 22 2013 issued in corresponding U.S. Appl. No. 12/714,827.
Extended Supplementary European Search Report dated Feb. 5, 2013 issued in corresponding Application No. / Patent No. 10818721.2-1526 / 2481444 PCT/JP2010065851.
3. Extended Supplementary European Search Report dated Apr. 29, 2013 issued in Application No./Patent No. 10818652.9-1660 / 2481336 PCT/JP2010064674.
Extended Supplementary European Search Report dated Apr. 26, 2013 issued in Application No./Patent No. 10818781.6-1506 / 2481355 PCT/JP2010063321.
U.S. Non-Final Office Action dated May 21, 2013 issued in corresponding U.S. Appl. No. 12/757,210.
U.S. Non-Final Office Action dated Jan. 29, 2014 issued in related U.S. Appl. No. 12/714,827.

* cited by examiner

SPACE ENSURING DEVICE

BACKGROUND OF THE INVENTION

1. Field of the Invention

The present invention relates to space ensuring devices.

This application claims the benefit of U.S. Provisional Application No. 61/244586, filed Sep. 22, 2009, which is hereby incorporated by reference herein in its entirety.

This application claims the priority under 35 U.S.C. §119 to Japanese Patent Application No. 2010-119749, filed May 25, 2010, which is hereby incorporated by reference herein in its entirety.

2. Description of Related Art

Conventionally known pericardioscopic procedures include those of the type in which an endoscope and a surgical instrument are inserted into the pericardial space from immediately under the xiphoid process and stem cells or the like are injected into an affected area (e.g., a boundary area between a myocardial infarction area and a normal area) without performing open heart surgery (e.g., see United States Patent Application, Publication No. 2004/0064138 A1).

In the pericardioscopic procedure described in United States Patent Application, Publication No. 2004/0064138 A1, a pressing force in the direction from the pericardium toward the heart is constantly applied to the endoscope inserted into the pericardial space, which restricts the operation of the endoscope.

BRIEF SUMMARY OF THE INVENTION

An object of the present invention is to provide a space ensuring device with which, in a pericardioscopic procedure, without providing an endoscope or surgical instrument with special space ensuring means and without unnecessarily dilating the pericardial space, it is possible to ensure a space necessary for operation of the endoscope or surgical instrument, so that maneuverability can be improved while suppressing complications, such as cardiac tamponade.

In order to achieve the above object, the present invention provides the following solution.

A first aspect of the present invention is a space ensuring device comprising: a pericardium pressing part for pressing a pericardium from the pericardial space side; a heart pressing part for pressing the surface of a heart from the pericardial space side; and an interconnecting part interconnecting the pericardium pressing part and the heart pressing part, wherein the interconnecting part generates the resilient force enabling expansion against a pressure applied by a pericardium and a heart so as to ensure a space between the pericardium pressing part and the heart pressing part.

A second aspect of the present invention is a space ensuring method comprising: inserting a space ensuring device according to claim 1 that is accommodated inside a guide tube into a pericardial space; and releasing the space ensuring device out of the guide tube to expand so as to ensure a space between a heart and a pericardium.

DETAILED DESCRIPTION OF THE INVENTION

A space ensuring device 1 according to a first embodiment of the present invention will be described below with reference to the drawings.

Figure 1:
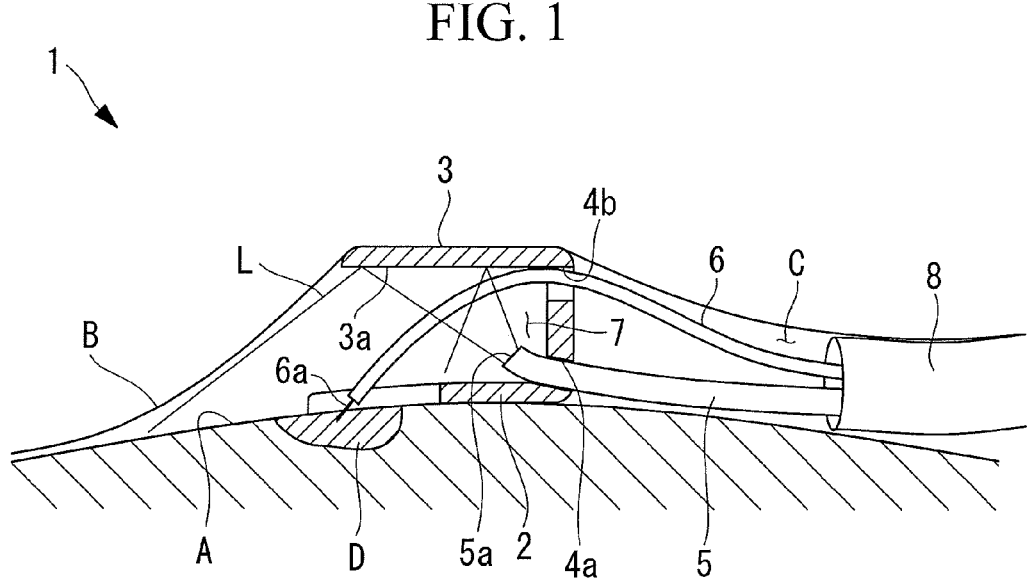
FIG. 1 is a longitudinal sectional view illustrating how a space ensuring device according to a first embodiment of the present invention is used in the pericardial space.

As shown in FIG. 1, the space ensuring device 1 according to this embodiment is a device that is placed in the pericardial space C located between the heart A and the pericardium B to widen the gap between the heart A and the pericardium B.

The space ensuring device 1 according to this embodiment is formed of an elastic material that can expand and contract, such as silicone resin. The space ensuring device 1 is an integrated unit including a heart pressing part 2 that comes into contact with the surface of the heart A, a pericardium pressing part 3 that comes into contact with the inner surface of the pericardium B, and an interconnecting part 4 interconnecting these pressing parts 2 and 3.

Figure 4:
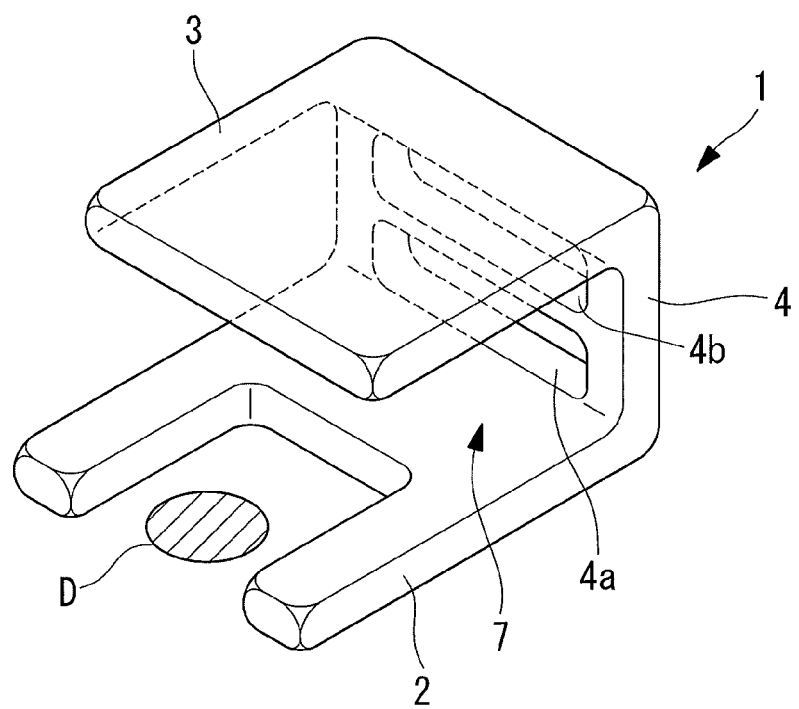
FIG. 4 is a perspective view illustrating the space ensuring device in FIG. 1.

As shown in FIG. 4, the heart pressing part 2 is a substantially U-shaped flat part. The heart pressing part 2 is placed at a position partially surrounding the periphery of a region that is to be observed with an endoscope 5 and treated with a surgical instrument 6 (e.g., an affected area D).

As shown in FIG. 4, the pericardium pressing part 3 is, for example, a rectangular flat part. As shown in FIG. 1, the pericardium pressing part 3 presses the pericardium B with its outer face. Furthermore, as shown in FIG. 1, the face of the pericardium pressing part 3 opposite the outer face is coated with a reflecting film 3a so that light L can be reflected therefrom.

The interconnecting part 4 is a part interconnecting one end of the heart pressing part 2 and one end of the pericardium pressing part 3. The interconnecting part 4 has a penetrating hole 4a that enables insertion of the endoscope 5 and a penetrating hole 4b that enables insertion of the surgical instrument 6.

The penetrating hole 4a for the endoscope 5 is inclined in a direction away from the heart pressing part 2 from the outside of the space ensuring device 1 into a space 7 formed between the heart pressing part 2 and the pericardium pressing part 3. Thus, it is possible to readily orient a distal-end face 5a of the endoscope 5 obliquely upward. The penetrating hole 4b for the surgical instrument 6 may be inclined in a direction away from the pericardium pressing part 3 from the outside of the space ensuring device 1 into the space 7.

Figure 2:
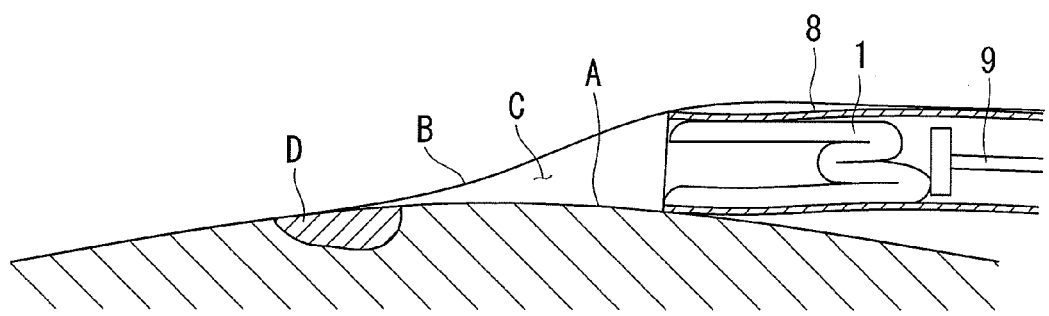
FIG. 2 is a longitudinal sectional view illustrating a contracted state of the space ensuring device in FIG. 1.
Figure 3:
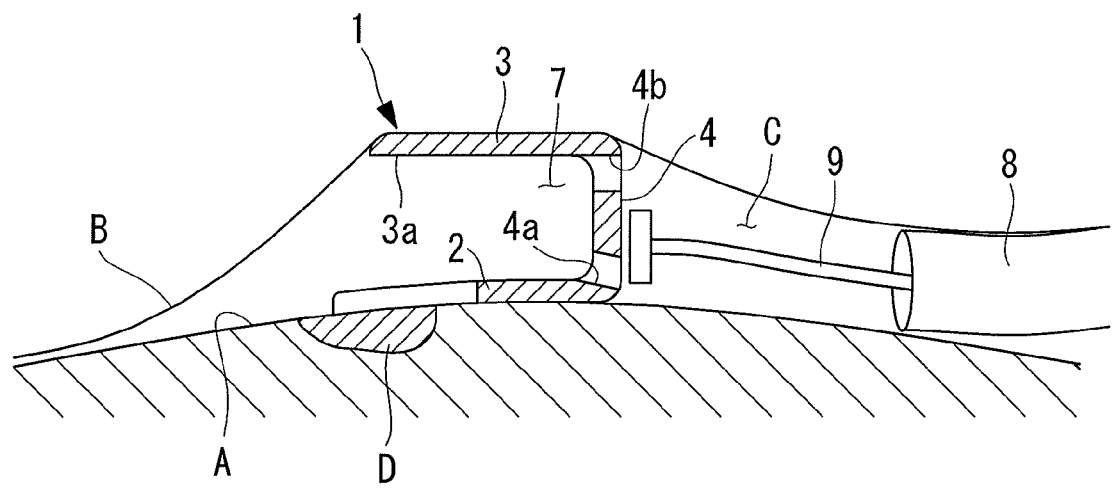
FIG. 3 is a longitudinal sectional view illustrating an expanded state of the space ensuring device in FIG. 1.

The space ensuring device 1 according to this embodiment can expand and contract between a contracted state in which, for example, the space ensuring device 1 can be accommodated inside a sheath (guide tube) 8 inserted from the bottom of the xiphoid process into the pericardial space C, as shown in FIG. 2, and an expanded state in which the space ensuring device 1 is freed by being pushed out of the sheath 8 with a push-out rod 9 inserted into the sheath 8 from the proximal end, as shown in FIG. 3. In the expanded state, the space ensuring device 1 expands by means of a preset resilient force. Thus, the space ensuring device 1 forms a sufficient space 7 without unnecessarily widening the gap between the pericardium B and the heart A.

The operation of the thus-configured space ensuring device 1 according to this embodiment will be described below.

In order to perform a procedure for injecting stem cells or the like while observing the affected area D (e.g., a boundary area between a myocardial infarction area and a normal area) with the space ensuring device 1 according to this embodiment, as shown in FIG. 2, the distal end of the sheath 8 accommodating the space ensuring device 1 in the contracted state in the vicinity of the distal end is inserted into the pericardial space C from the bottom of the xiphoid process or the like. In this state, the region where the pericardium B and the heart A are separated from each other is restricted to the vicinity of the distal end of the sheath 8.

In this state, as shown in FIG. 3, the space ensuring device 1 accommodated inside the sheath 8 is pushed out of the sheath 8 by the push-out rod 9 introduced from the proximal end of the sheath 8. At this time, as shown in FIG. 4, the heart pressing part 2 is placed at a position surrounding the affected area D. Since the space ensuring device 1 is formed of an elastic material, the space ensuring device 1 expands by means of its resilient force. Thus, the pericardium pressing part 3 presses the pericardium B, and the heart pressing part 2 presses the heart A, whereby it is possible to widen the gap between the pericardium B and the heart A in the vicinity of the affected area D.

At this time, in the expanded state, the space ensuring device 1 expands by means of its preset resilient force. Thus, it is possible to form a sufficient space 7 without unnecessarily widening the gap between the pericardium B and the heart A.

Then, the endoscope 5 and the surgical instrument 6 are introduced into the pericardial space C via the sheath 8. Then, the endoscope 5 is inserted into the space 7 formed between the heart pressing part 2 and the pericardium pressing part 3 via the penetrating hole 4a on the side of the heart A provided on the interconnecting part 4, whereas the surgical instrument 6 is inserted into the space 7 via the penetrating hole 4b on the side of the pericardium B.

The penetrating hole 4a for the endoscope 5 is inclined in a direction away from the heart pressing part 2 into the space 7. Therefore, the endoscope 5 inserted through the penetrating hole 4a is readily guided so that the distal-end face 5a thereof becomes oriented obliquely upward. Then, as shown in FIG. 1, illuminating light is radiated from the distal-end face 5a. The illuminating light is reflected toward the surface of the heart A by the reflecting surface 3a provided on the pericardium pressing part 3 and illuminates the surface of the heart A. Meanwhile, return light returning from the surface of the heart A, such as fluorescence and reflected light, is collected by an objective lens (not shown) provided on the distal-end face 5a of the endoscope 5 via the reflecting surface 3a.

In this case, the light path from the distal-end face 5a of the endoscope 5 to the surface of the heart A is reflected back at the reflecting surface 3a. Thus, it is possible to ensure a distance from the distal-end face 5a of the endoscope 5 to the surface of the heart A without unnecessarily widening the gap between the pericardium B and the heart A. Therefore, it is possible to sufficiently illuminate and observe the affected area D without excessively spreading the illuminating light. Accordingly, for example, it is possible to suppress complications, such as cardiac tamponade.

Then, in this state, as shown in FIG. 1, it is possible to reliably puncture the boundary area between the affected area D and the normal area with an injection needle 6a at the distal end of the surgical instrument 6 and inject stem cells or the like while observing with the endoscope 5 the surgical instrument 6 introduced into the space 7 via the penetrating hole 4b on the side of the pericardium B of the interconnecting part 4.

After completing observation and the procedure, it is possible to readily withdraw the space ensuring device 1 by holding it with forceps (not shown) introduced via the sheath 8 and pulling it into the sheath 8 while deforming it.

In this embodiment, in the case where the penetrating hole 4b for inserting the surgical instrument 6 is inclined in a direction away from the pericardium pressing part 3 from the outside of the space ensuring device 1 into the space 7, an advantage is afforded in that it is possible to readily guide the injection needle 6a at the distal end of the surgical instrument 6 to the affected area D.

Furthermore, in this embodiment, since the reflecting surface 3a reflects light returning from an area including the affected area D, the acquired image is a reversed image. Thus, preferably, image reversal processing is performed by an image processing unit (not shown) connected to the proximal end of the endoscope 5.

Furthermore, although this embodiment has been described in the context of an example where the entire device 1 is formed of silicone resin, alternatively, the device 1 may be formed of other elastic materials, such as polyurethane resin. Furthermore, by adjusting the compliance with the heart A and the pericardium B, the space ensuring device 1 according to this embodiment can function as a part that restrains forces applied due to the effects of the pulsation of the heart A or breathing. Specifically, the heart pressing part 2, which comes into contact with the heart A, may be formed of a material that is flexible and readily restores its shape, such as silicone resin or polyurethane resin, whereas the pericardium pressing part 3, which comes into contact with the pericardium B, may be formed of a material that is rigid and does not easily deform, such as PTFE or polyethylene. Alternatively, the composition may be the opposite.

Furthermore, although the space ensuring device 1 in the contracted state accommodated inside the sheath 8 is expanded in the pericardial space C by pushing it out of the sheath 8 in the embodiment described above, alternatively, the space ensuring device 1 in the contracted state accommodated in a forceps channel (not shown) provided in the endoscope 5 may be pushed out of the forceps channel.

Furthermore, preferably, a material that does not transmit X rays is mixed in the silicone resin or the like constituting the space ensuring device 1. Accordingly, it is possible to readily confirm the position of the space ensuring device 1 in the pericardial space C by viewing a radiographic image.

Next, a space ensuring device 10-1 according to a second embodiment of the present invention will be described below with reference to the drawings.

In the description of the space ensuring device 10-1 according to this embodiment, parts that are configured the same as those of the space ensuring device 1 according to the first embodiment described above will be designated by the same reference signs, and a description thereof will be omitted.

Figure 5:
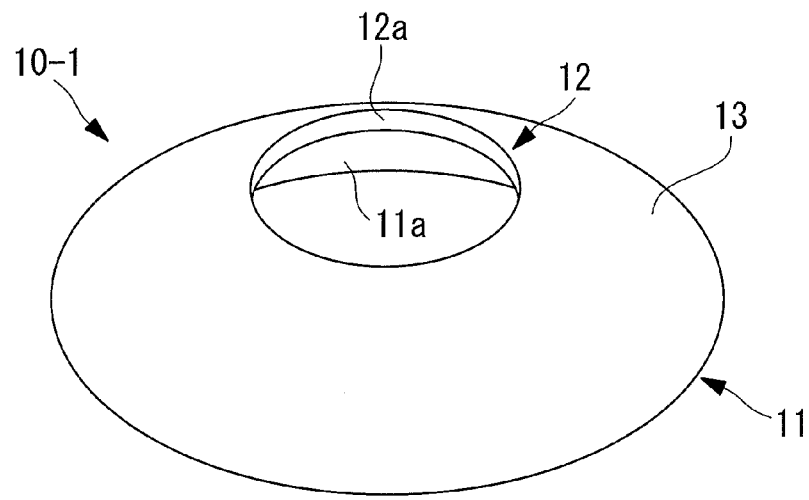
FIG. 5 is a perspective view illustrating a space ensuring device according to a second embodiment of the present invention.
Figure 6:
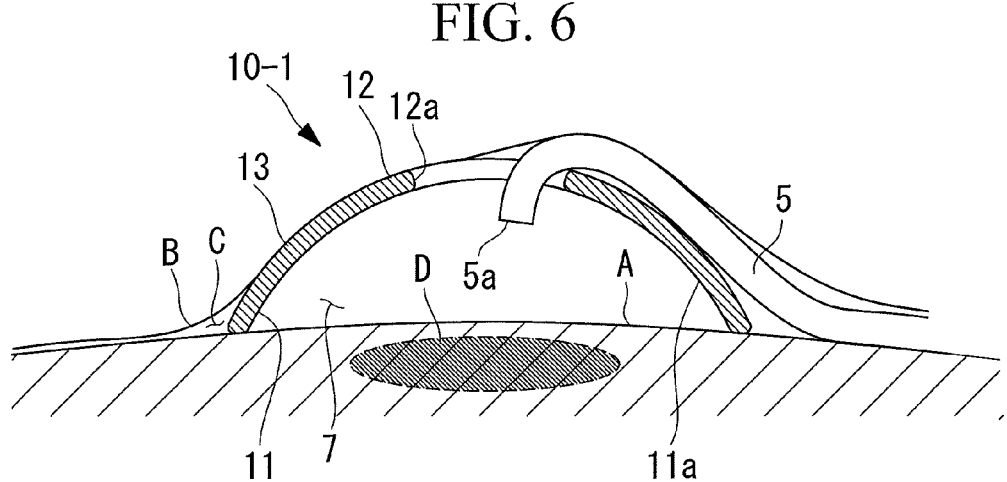
FIG. 6 is a longitudinal sectional view illustrating how the space ensuring device in FIG. 5 is used in the pericardial space.

As shown in FIGS. 5 and 6, the space ensuring device 10-1 according to this embodiment is a cup-shaped device. The space ensuring device 10-1 has a heart pressing part 11 having a wide heart-side opening 11a, a pericardium pressing part 12 having a narrow pericardium-side opening 12a, and a ring-shaped interconnecting part 13 interconnecting these pressing parts 12 and 13. The space ensuring device 10-1 is formed of an elastic material, such as silicone resin.

The pericardium-side opening 12a has a sufficient diameter for introducing the distal end of the endoscope 5 from outside to inside. The heart-side opening 11a has a sufficient diameter for surrounding the affected area D that is to be observed and treated.

The interconnecting part 13 on its outer side has an outward convex spherical outer surface.

The space ensuring device 10-1 according to this embodiment also can be deformed between a contracted state, in which the space ensuring device 10-1 can be accommodated inside the sheath 8, and an expanded state, in which the space ensuring device 10-1 is freed from the sheath 8 and expands to widen the gap between the surface of the heart A and the pericardium B.

The operation of the thus-configured space ensuring device 10-1 according to this embodiment will be described below.

In order to observe and treat the affected area D of the heart A with the space ensuring device 10-1 according to this embodiment, similarly to the first embodiment, the sheath 8 accommodating the space ensuring device 10-1 in the contracted state is inserted into the pericardial space C, and the space ensuring device 10-1 is pushed out of the sheath 8, whereby the space ensuring device 10-1 expands with the heart-side opening 11a placed at a position surrounding the affected area D. Thus, the heart pressing part 11 comes into tight contact with the surface of the heart A, whereby the heart-side opening 11a is closed by the surface of the heart A. On the other hand, the pericardium pressing part 12 comes into tight contact with the inner surface of the pericardium B, whereby the pericardium-side opening 12a is closed by the inner surface of the pericardium B.

Then, the endoscope 5 introduced into the pericardial space C via the sheath 8 is advanced over the outer surface of the space ensuring device 10-1. Thus, as shown in FIG. 6, it is possible to slide the endoscope 5 between the pericardium B, which closes the pericardium-side opening 12a, and the pericardium pressing part 12 and to readily advance the distal end thereof into the space 7 via the pericardium-side opening 12a.

Accordingly, the distal end of the endoscope 5 is placed at a position sufficiently separated from the surface of the heart A, so that it is possible to freely curve a curving portion thereof in the space 7. Therefore, an advantage is afforded in that it is possible to readily observe the affected area D without compromising the maneuverability of the endoscope 5. Furthermore, an advantage is afforded in that it is possible to readily perform a procedure with the surgical instrument 6 introduced separately from the endoscope 5 or via the forceps channel of the endoscope 5.

Furthermore, with the space ensuring device 10-1 according to this embodiment, since the outer surface thereof is an outward convex curved surface, it is easy to curve the endoscope 5 following the outer surface. Accordingly, the operation of the endoscope 5 at the time of advancement through the pericardium-side opening 12a can be facilitated.

Figure 7:
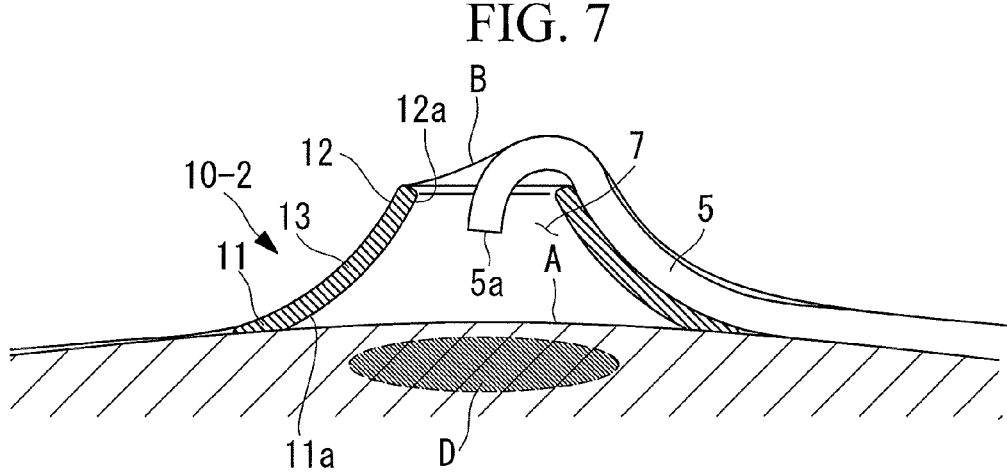
FIG. 7 is a longitudinal sectional view illustrating a modification of the space ensuring device in FIG. 5.

Instead of the outward convex curved shape, as shown in FIG. 7, the curved surface may have an outward concave shape.

Accordingly, it is possible to restrict the inclination angle of the outer surface of the interconnecting part 13 at the position rising from the surface of the heart A, so that an advantage is afforded in that it is possible to readily move the endoscope 5 onto the outer surface of a space ensuring device 10-2.

Figure 8:
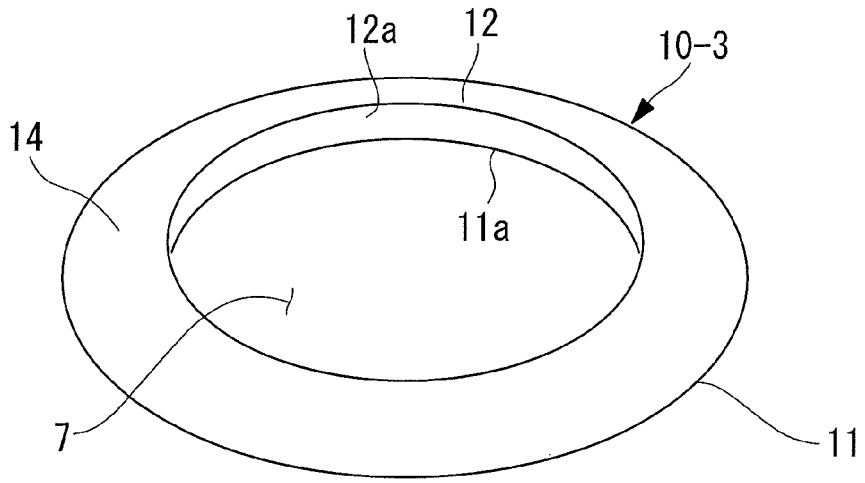
FIG. 8 is a perspective view illustrating another modification of the space ensuring device in FIG. 5.
Figure 9:
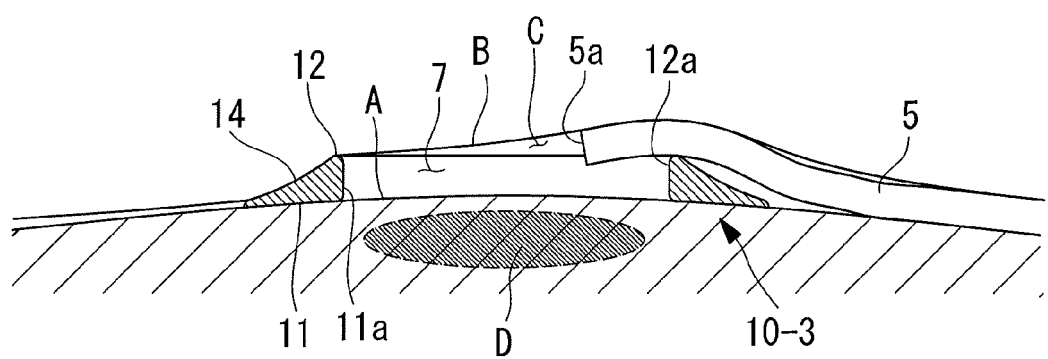
FIG. 9 is a longitudinal sectional view illustrating how the space ensuring device in FIG. 8 is used in the pericardial space.

Furthermore, although the space ensuring devices 10-1 and 10-2 shown in FIGS. 6 and 7 are shaped like thin cylinders, alternatively, as shown in FIGS. 8 and 9, a ring-shaped space ensuring device 10-3 having a triangular cross section may be adopted. Also in this case, the outer surface may be an inclined surface 14 so that the space ensuring device 10-3 becomes thicker from the outer circumference toward the inner circumference.

Figure 10:
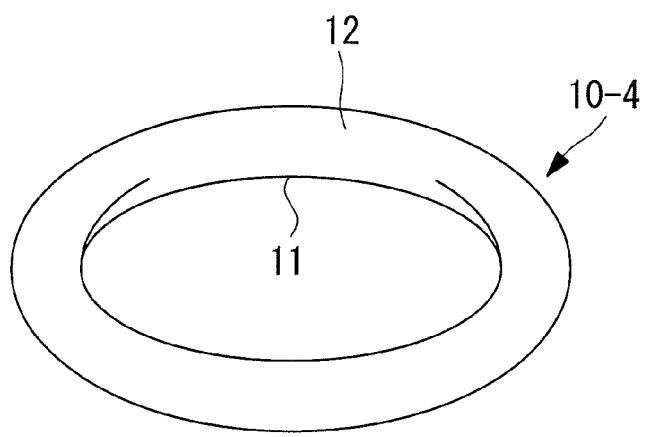
FIG. 10 is a perspective view illustrating another modification of the space ensuring device in FIG. 5.
Figure 11:
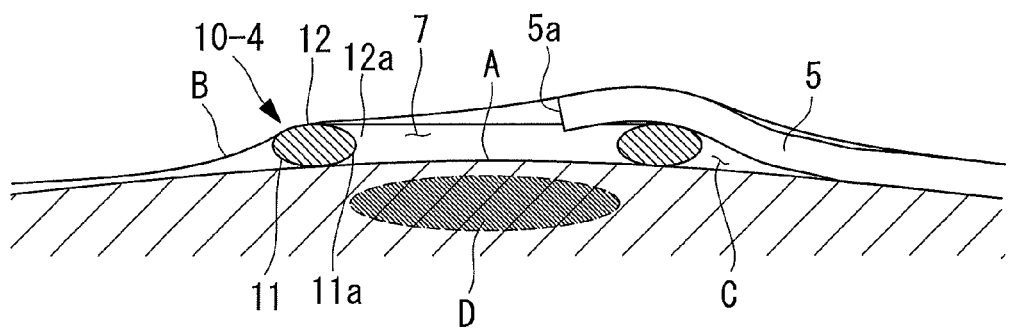
FIG. 11 is a longitudinal sectional view illustrating how the space ensuring device in FIG. 10 is used in the pericardial space.

Alternatively, as shown in FIG. 10, a ring-shaped space ensuring device 10-4 simply having a circular or substantially elliptic cross section may be adopted. Also in this case, as shown in FIG. 11, it is possible to readily ensure a certain space 7 for operation of the endoscope 5 between the pericardium B and the surface of the heart A. In order to facilitate holding at the time of withdrawal, a handle (not shown) projecting outward may be provided.

Figure 12:
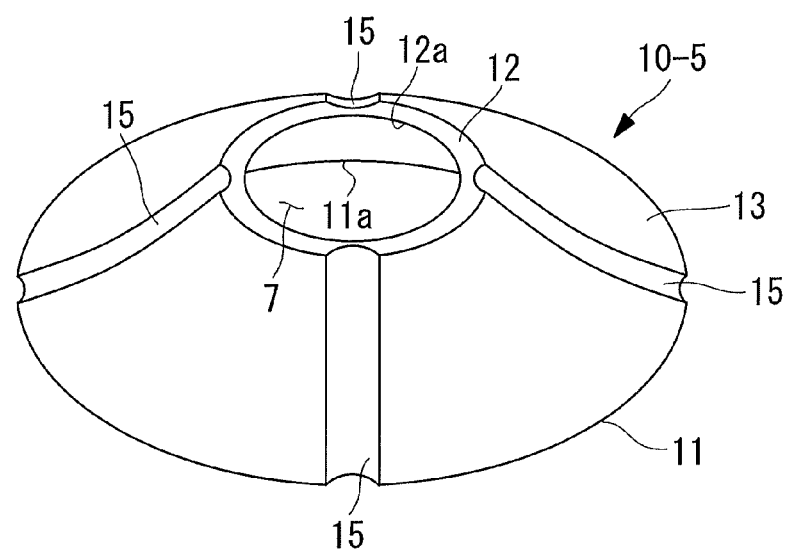
FIG. 12 is a perspective view illustrating another modification of the space ensuring device in FIG. 5.
Figure 13:
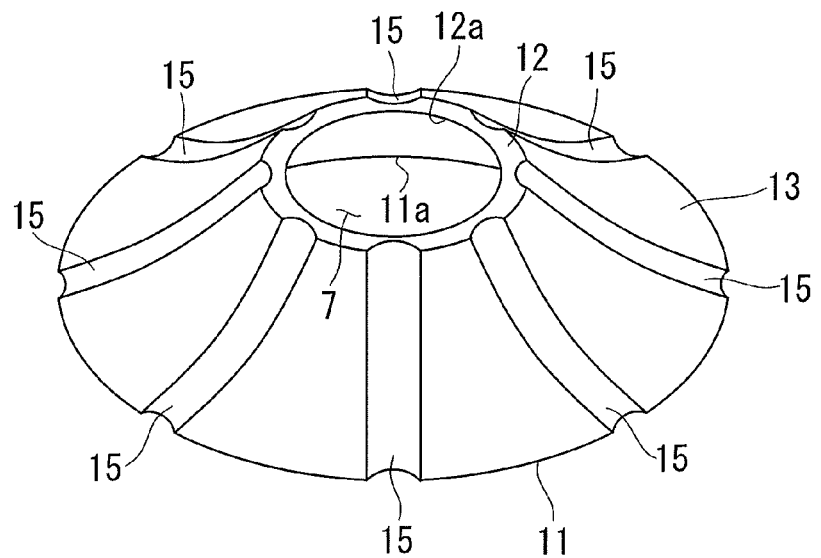
FIG. 13 is a perspective view illustrating another modification of the space ensuring device similar to the one in FIG. 12.

Alternatively, as shown in FIGS. 12 and 13, a space ensuring device 10-5 having one or more grooves 15 extending so as to connect the outer circumference and the inner circumference on the outer surface of the interconnecting part 13 may be adopted. Accordingly, an advantage is afforded in that it is possible to readily introduce the endoscope 5 into the internal space 7 via the pericardium-side opening 12a.

Figure 14:
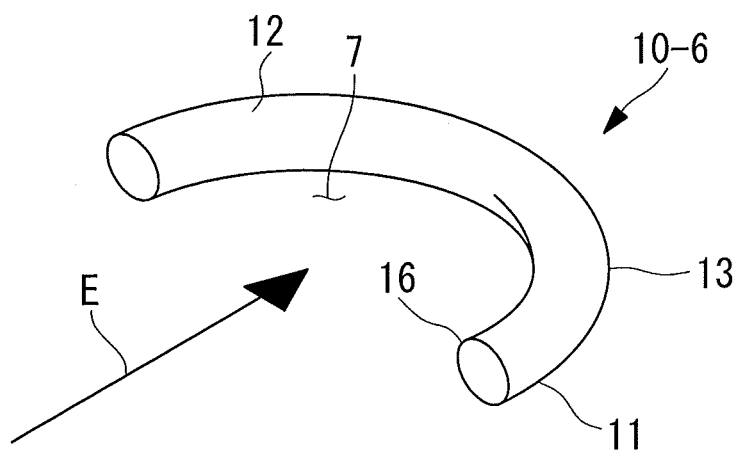
FIG. 14 is a perspective view illustrating another modification of the space ensuring device in FIG. 5.
Figure 15:
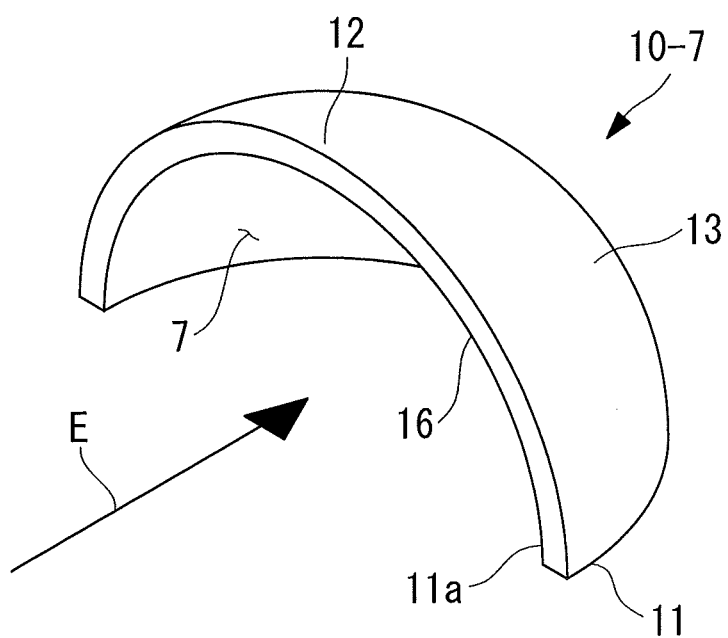
FIG. 15 is a perspective view illustrating another modification of the space ensuring device in FIG. 5.

Alternatively, as shown in FIGS. 14 and 15, space ensuring devices 10-6 and 10-7 in which the heart pressing part 11 is not closed like a ring but has a substantially U shape may be adopted. Space ensuring devices 10-6 may be hollow.

In this case, the interconnecting part 13 is partially open to form an opening 16. Thus, as indicated by arrows E in the figures, it is possible to introduce the endoscope 5 or the surgical instrument 6 into the space 7 surrounded by the space ensuring device 10 via the opening 16.

Figure 16:
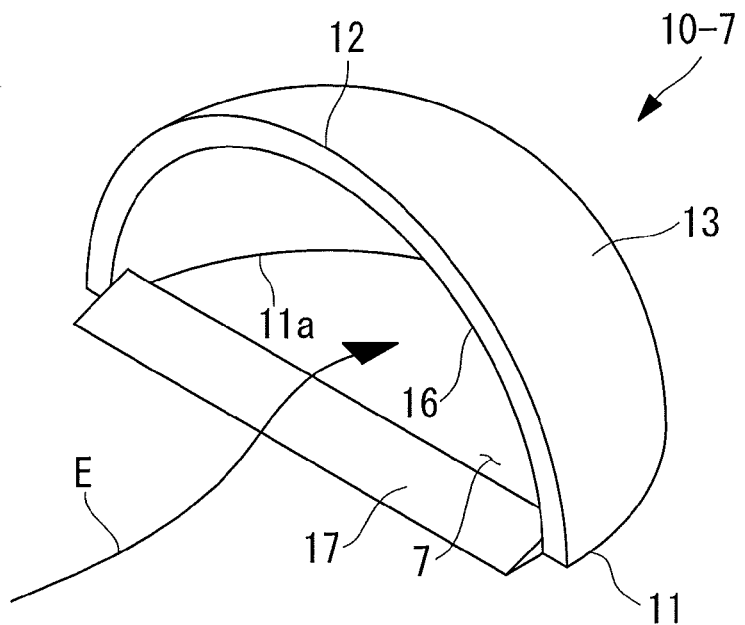
FIG. 16 is a perspective view illustrating a modification of the space ensuring device in FIG. 15.
Figure 17:
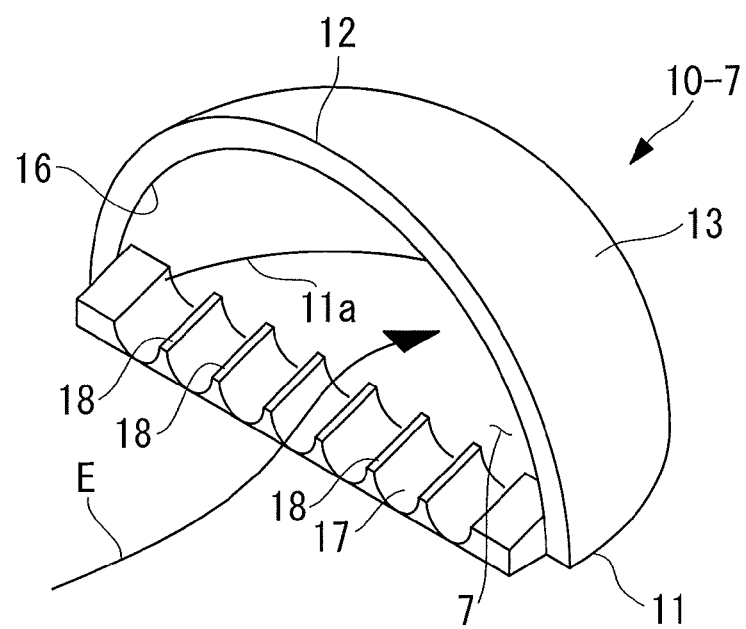
FIG. 17 is a perspective view illustrating a modification of the space ensuring device in FIG. 16.

Alternatively, as shown in FIGS. 16 and 17, an inclined surface (guide table) 17 may be provided at the heart pressing part 11 in the space ensuring device 10-7 so that the distal end of the endoscope 5 introduced into the space 7 floats above the surface of the heart A. In the example shown in FIG. 17, grooves 18 are provided on the inclined surface 17. By holding the endoscope 5 or the surgical instrument 6 in the grooves 18, it is possible to stabilize the endoscope 5 or the surgical instrument 6 during operation.

Figure 18:
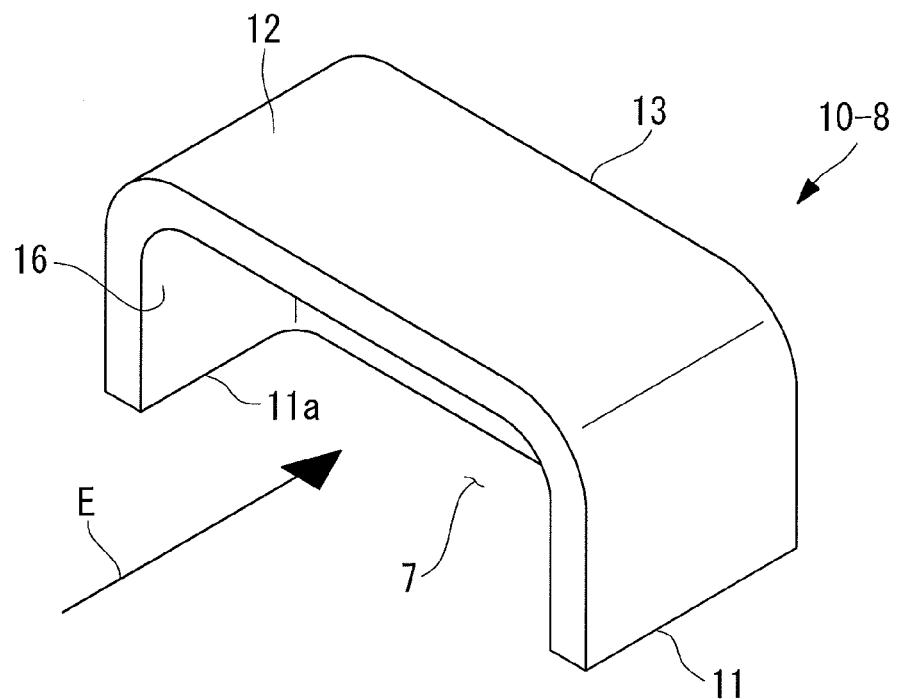
FIG. 18 is a perspective view illustrating another modification of the space ensuring device in FIG. 15.
Figure 19:
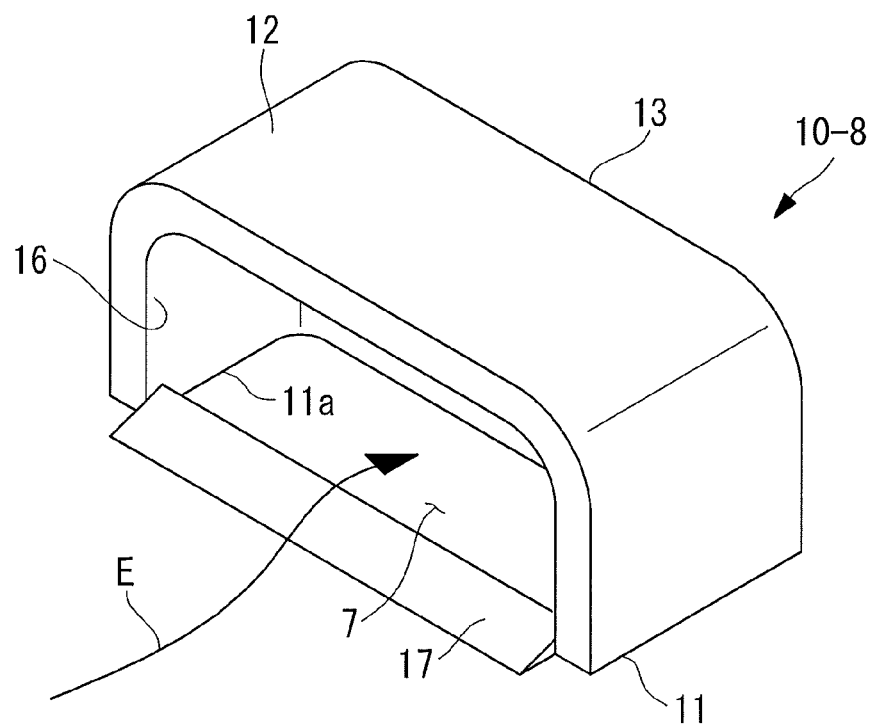
FIG. 19 is a perspective view illustrating another modification of the space ensuring device in FIG. 18.

Alternatively, as shown in FIGS. 18 and 19, a space ensuring device 10-8 in which the substantially U-shaped heart pressing part 11 has a rectangular shape instead of a circular shape may be adopted. FIG. 19 is an example where an inclined surface 17 with which the distal end of the endoscope 5 introduced into the space 7 floats above the surface of the heart A is provided at the heart pressing part 11. The inclined surface 17 may have grooves 18 similar to those shown in FIG. 17.

Figure 20:
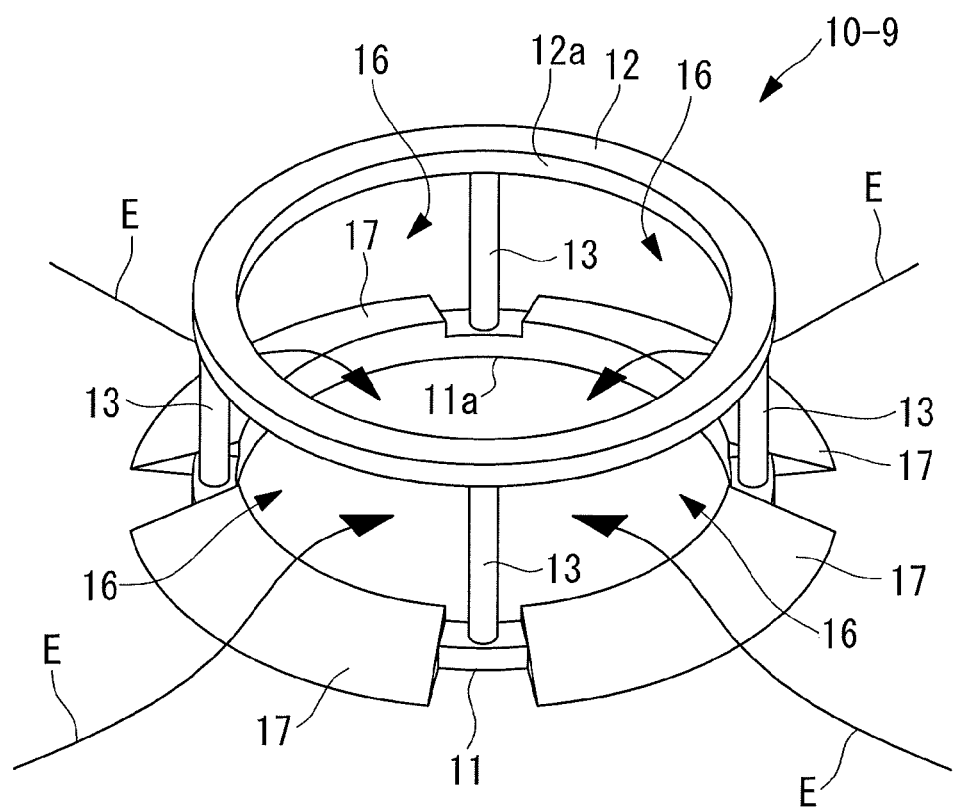
FIG. 20 is a perspective view illustrating another modification of the space ensuring device in FIG. 5.
Figure 21:
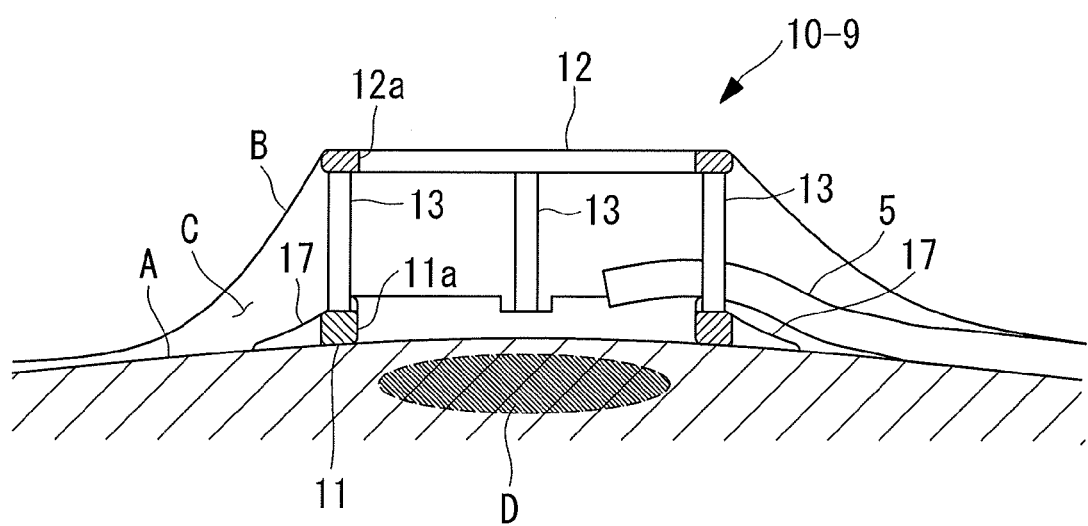
FIG. 21 is a longitudinal sectional view illustrating how the space ensuring device in FIG. 20 is used in the pericardial space.
Figure 22:
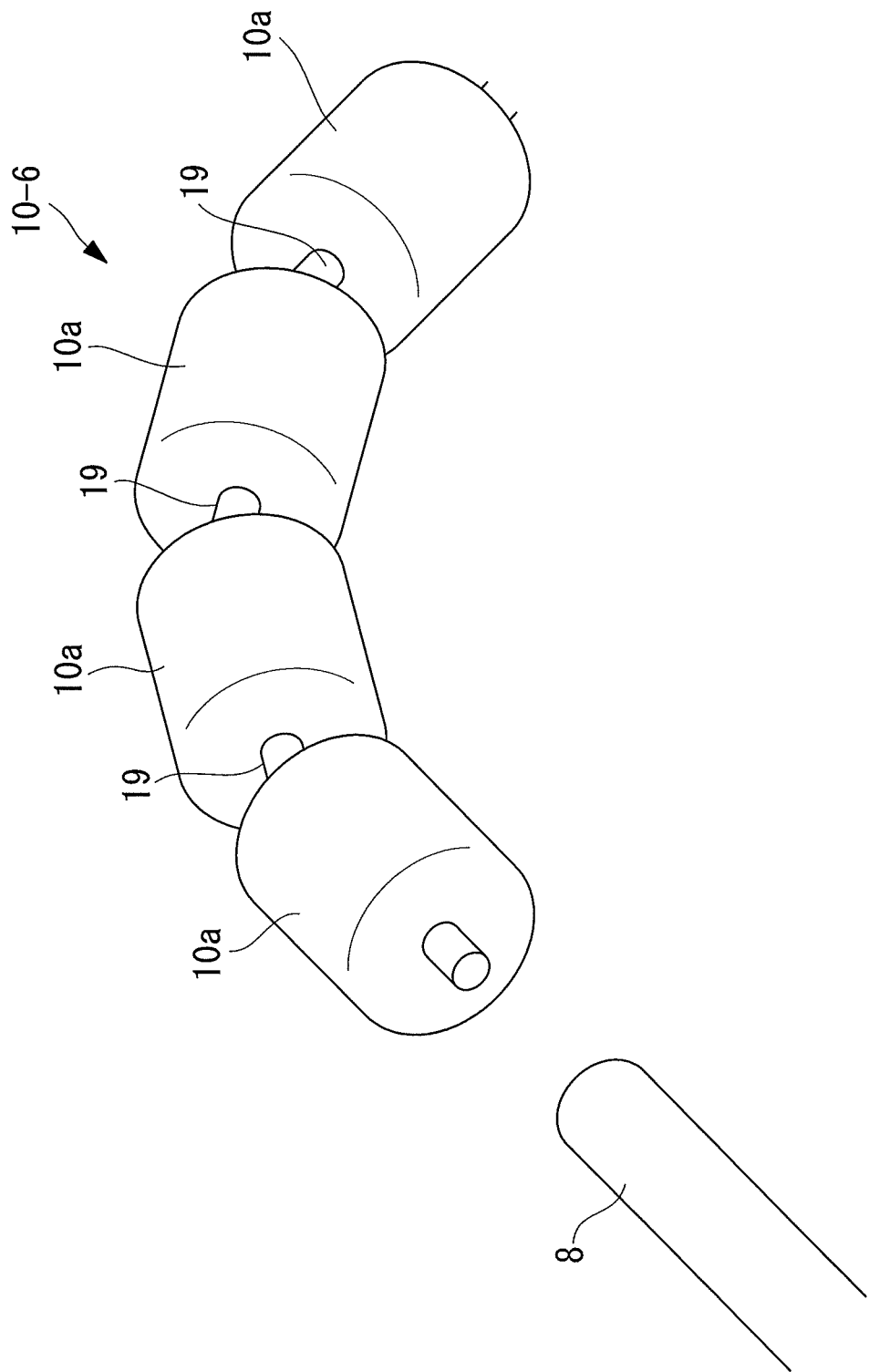
FIG. 22 is a perspective view illustrating a modification of the space ensuring device in FIG. 14.

Alternatively, as shown in FIGS. 20 and 21, a basket-shaped space ensuring device 10-9 may be constructed by forming the interconnecting part 13 with a plurality of support rods. In the example shown in FIGS. 20 and 21, inclined surfaces 17 are provided on the heart pressing part 11 in association with individual openings 16 provided between the support rods constituting the interconnecting part 13. Accordingly, it is possible to float the endoscope 5 or the like introduced into the internal space 7 from the surface of the heart A.

Figure 23:
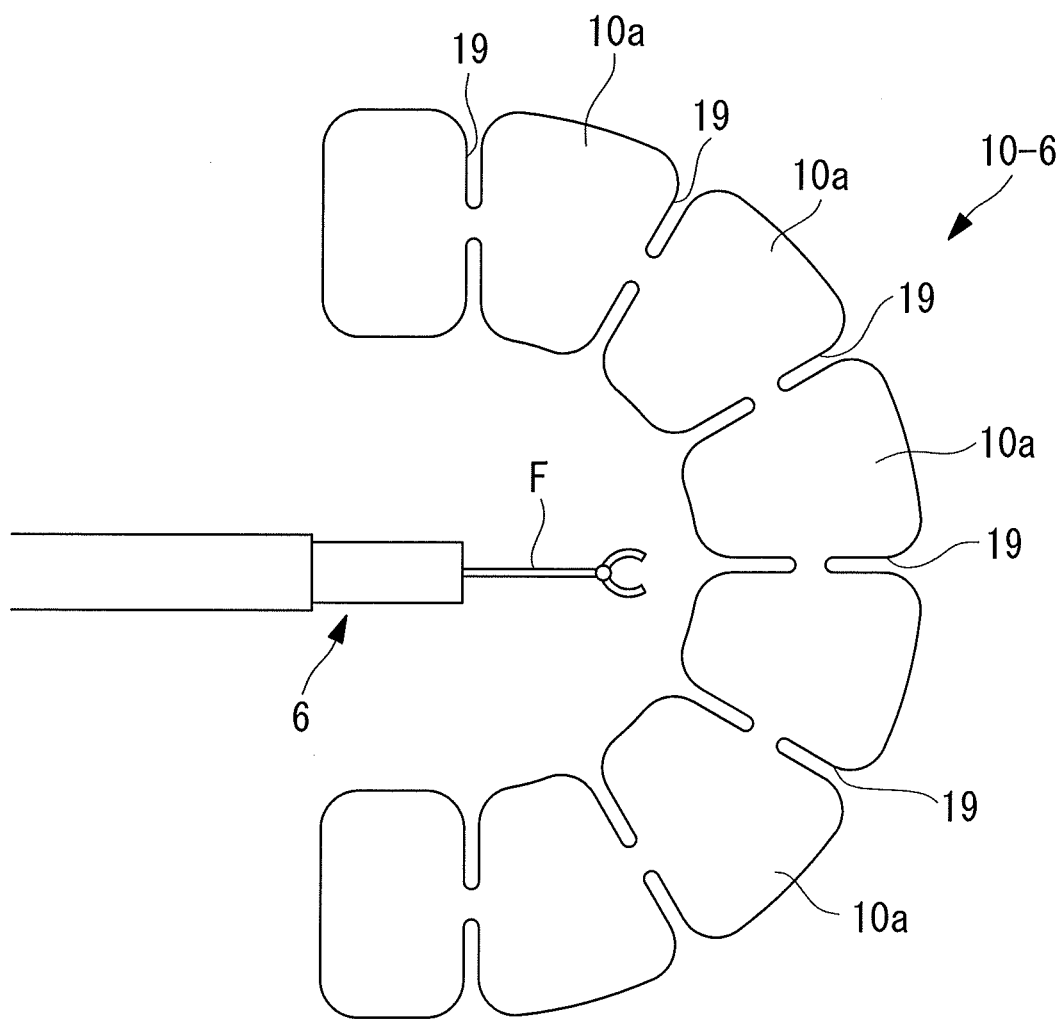
FIG. 23 is a plan view illustrating a modification of the space ensuring device in FIG. 14.
Figure 24:
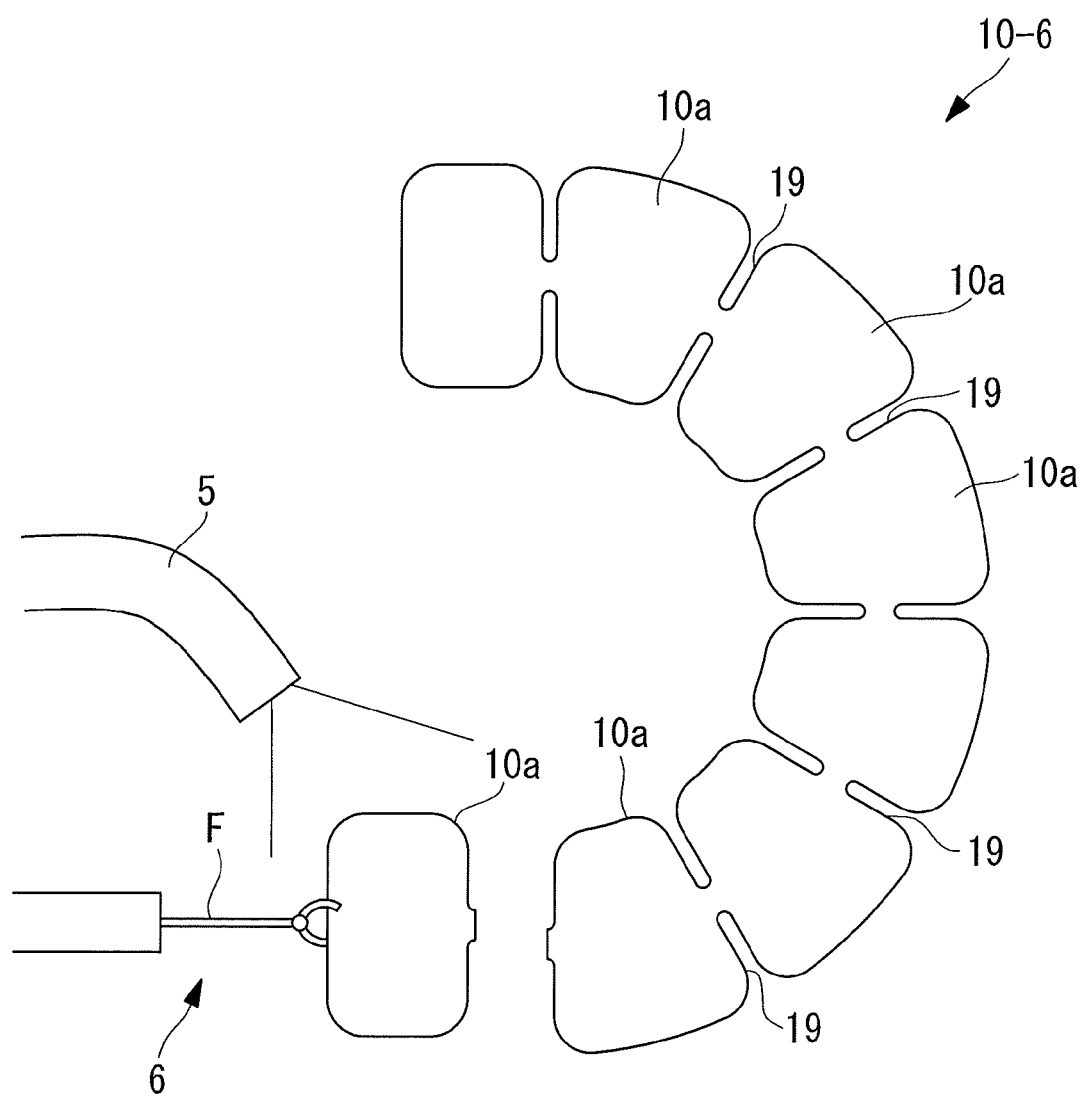
FIG. 24 is a plan view illustrating a task of withdrawing the space ensuring device in FIG. 23.

Furthermore, as shown in FIGS. 23 and 24, a space ensuring device (the space ensuring device 10-6 is used as an example here) having division lines 19 for dividing the space ensuring device 10-6 into a plurality of segments 10a may be adopted. The cross sectional area of the space ensuring device 10-6 is sufficiently small at the positions of the division lines 19, so that it is readily possible to cut the space ensuring device 10-6 with forceps F or the like. As shown in FIG. 24, the segments 10a of the space ensuring device 10-6 that has been cut can be readily withdrawn into the sheath 8 while observing them with the endoscope 5. Thus, an advantage is afforded in that the withdrawing task can be facilitated. The division lines 19 may be applied to other space ensuring devices 1 and 10-1 to 10-9.

Furthermore, although the space ensuring devices 1 and 10-1 to 10-9 in the embodiments described above are formed of an elastic material, such as silicone resin, alternatively, as shown in FIGS. 25 to 30, space ensuring devices 30-1 to 30-3 configured of wires formed of a metallic material or a plastic material may be adopted.

Figure 25:
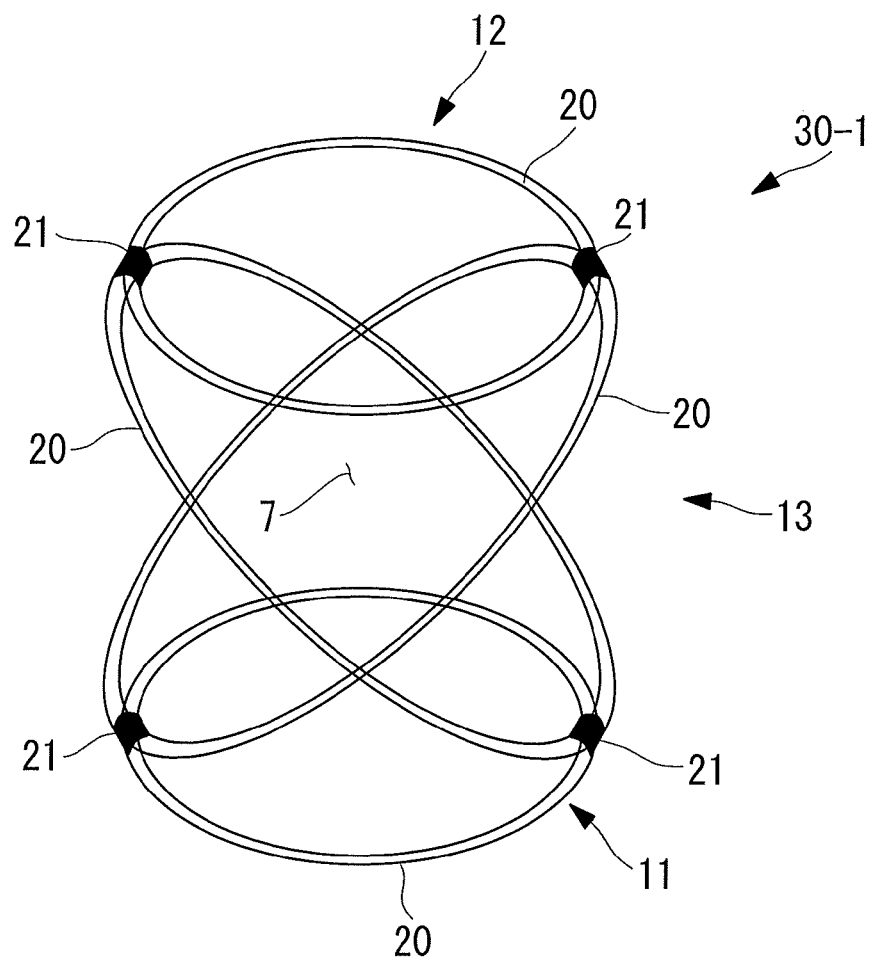
FIG. 25 is a perspective view illustrating an expanded state of another modification of the space ensuring device in FIG. 5.
Figure 26:
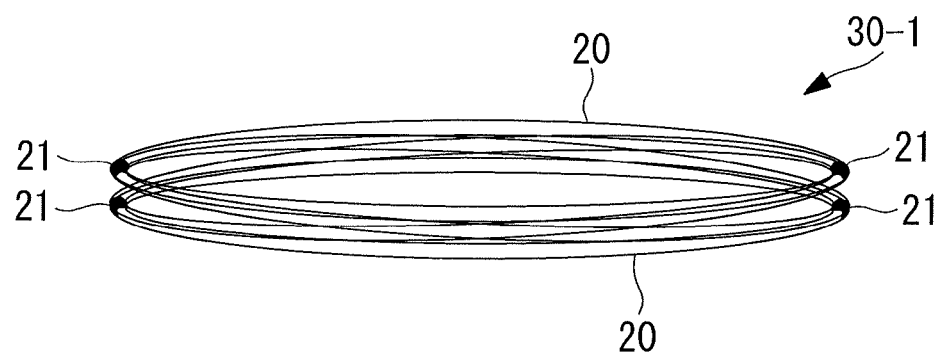
FIG. 26 is a perspective view illustrating a contracted state of the space ensuring device in FIG. 25.

For example, in the space ensuring device 30-1 shown in FIGS. 25 and 26, four ring-shaped wires 20 are connected via tubes 21 or the like in such a manner that the wires 20 can be moved relative to each other. The space ensuring device 30-1 is configured so that it can be deformed between a contracted state shown in FIG. 26 and an expanded state shown in FIG. 25.

That is, when in the contracted state shown in FIG. 26, the space ensuring device 30-1 can be readily introduced into the pericardial space C via the sheath 8 or the like. When freed from the sheath 8, as shown in FIG. 25, the space ensuring device 30-1 expands to widen the space 7 between the pericardium B and the heart A.

Alternatively, the wires 20 may be formed of a shape-memory material. In this case, for example, the space ensuring device 30-1 may be cooled inside the sheath 8 so that it is maintained in the contracted state shown in FIG. 26, whereas it enters the expanded state shown in FIG. 25 due to body temperature when introduced into the pericardial space C. The space ensuring device 30-1 can be cooled by using a Peltier device or by spraying a low-temperature medium, such as liquid nitrogen. Furthermore, the space ensuring device 30-1 enters the contracted state shown in FIG. 26 at the time of withdrawal simply by cooling, so that the space ensuring device 30-1 can be readily withdrawn.

Figure 27:
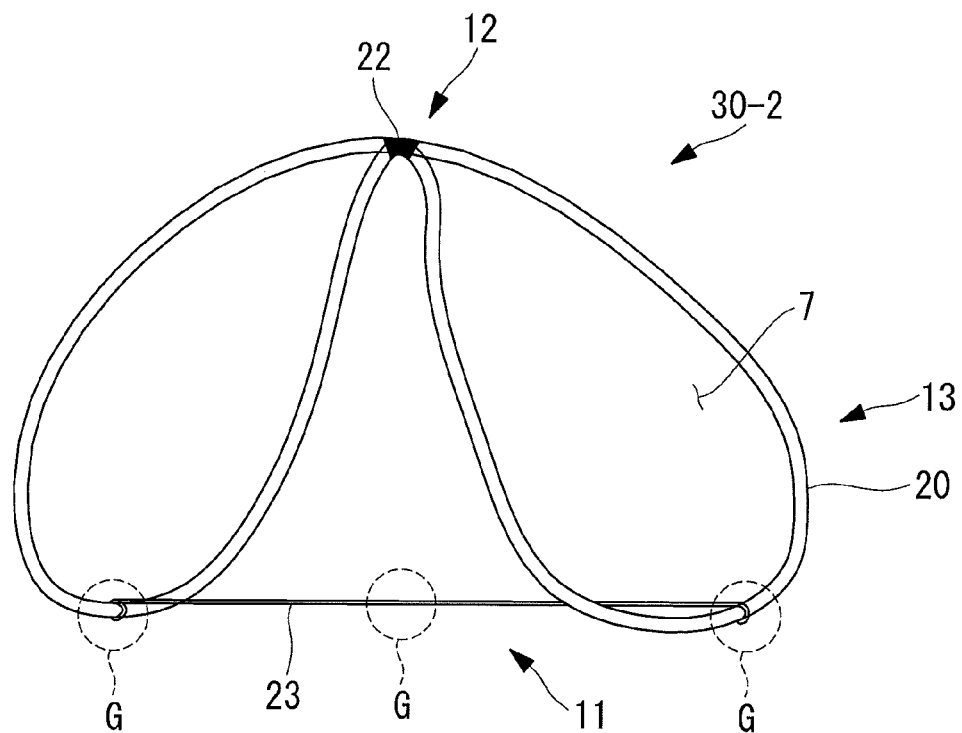
FIG. 27 is a perspective view illustrating an expanded state of a modification of the space ensuring device in FIG. 25.
Figure 28:
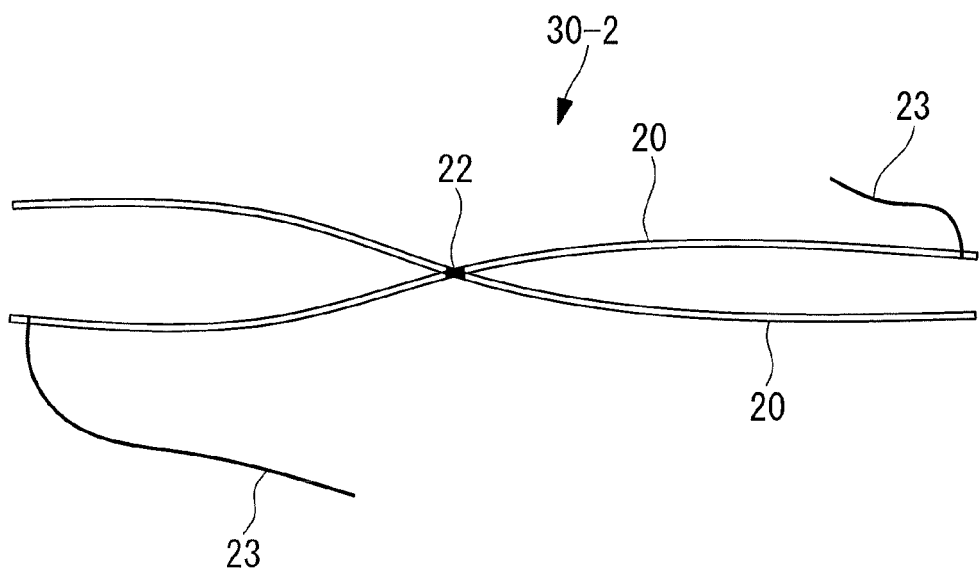
FIG. 28 is a plan view illustrating a contracted state of the space ensuring device in FIG. 27.

Alternatively, as shown in FIG. 27, a space ensuring device 30-2 having a structure in which a ring-shaped wire 20 formed of an elastic material is bundled at a junction 22 and both ends are connected via a thread 23 may be adopted. FIG. 27 shows an expanded state of the space ensuring device 30-2. By using the portion connected via the thread 23 as the heart pressing part 11 and the junction 22 as the pericardium pressing part 12, it is possible to form the space 7 stably in the pericardial space C. The space ensuring device 30-2 can be folded compactly by bending and can be readily accommodated inside the sheath 8. Meanwhile, at the time of withdrawal into the sheath 8, for example, the space ensuring device 30-2 is cut with the forceps F or the like at the positions surrounded by broken lines G in FIG. 27, whereby the space ensuring device 30-2 becomes thin and elongated and can be readily withdrawn into the sheath 8.

Figure 29:
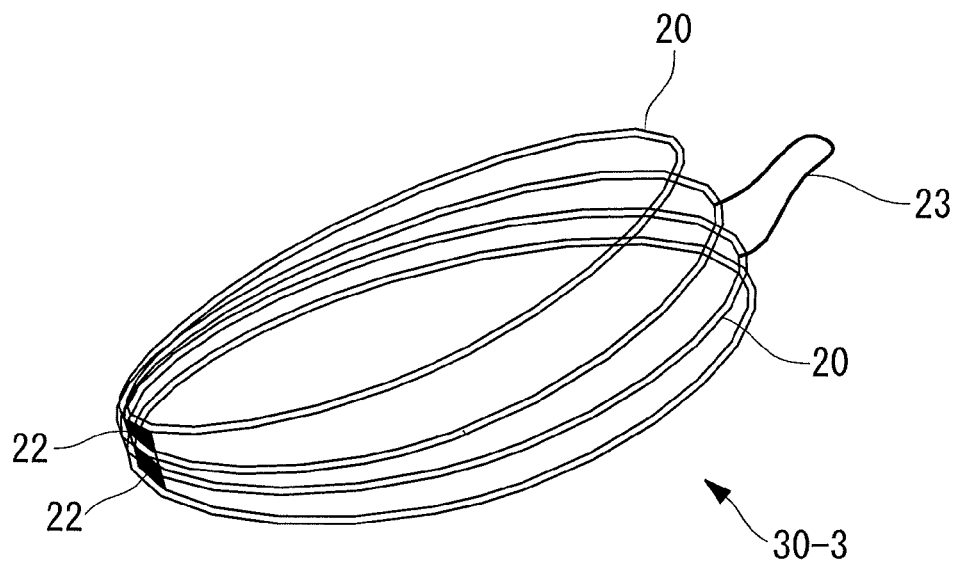
FIG. 29 is a perspective view illustrating a contracted state of a modification of the space ensuring device in FIG. 25.
Figure 30:
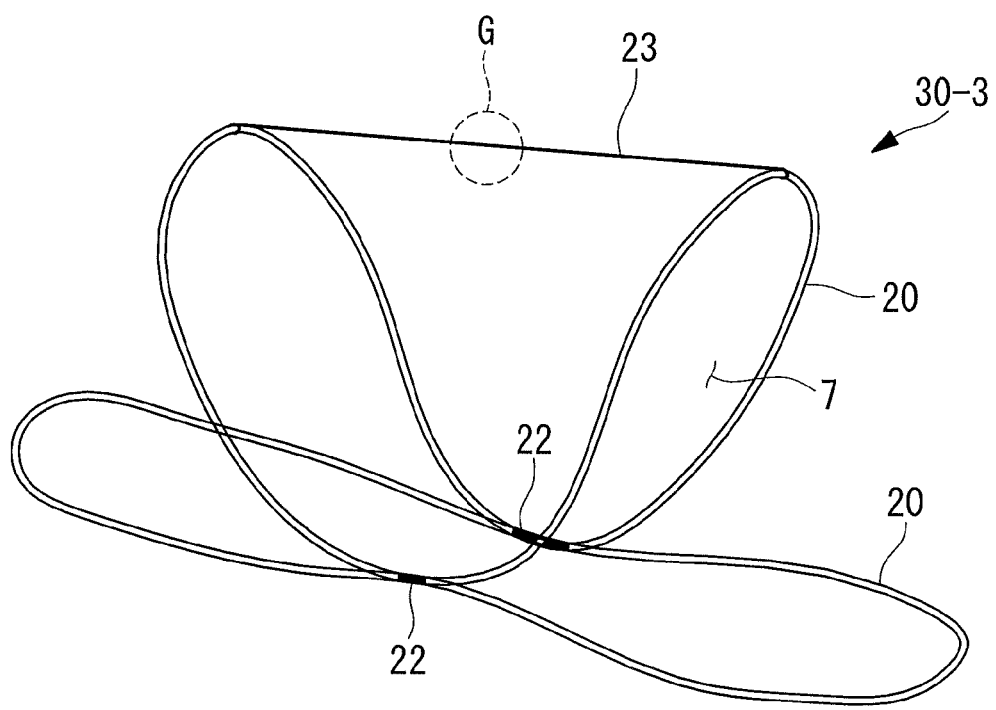
FIG. 30 is a perspective view illustrating an expanded state of the space ensuring device in FIG. 29.

Alternatively, as shown in FIGS. 29 and 30, a space ensuring device 30-3 having a structure in which two ring-shaped wires 20 formed of an elastic material are bundled at two junctions 22 and both ends of one of the wires 20 are connected via a thread 23 may be adopted. By using the ring-shaped wire 20 not connected via the thread 23 as the heart pressing part 11 and the portion connected via the thread 23 as the pericardium pressing part 12, it is possible to form the space 7 stably in the pericardial space C. As shown in FIG. 29, the space ensuring device 30-3 can be folded compactly by bending and can be readily accommodated inside the sheath 8. Meanwhile, at the time of withdrawal into the sheath 8, for example, the space ensuring device 30-3 is cut with the forceps F or the like at the position surrounded by a broken line G in FIG. 30, whereby the space ensuring device 30-3 becomes thin and elongated with the two ring-shaped wires simply overlapping and can be readily withdrawn into the sheath 8.

Figure 31:
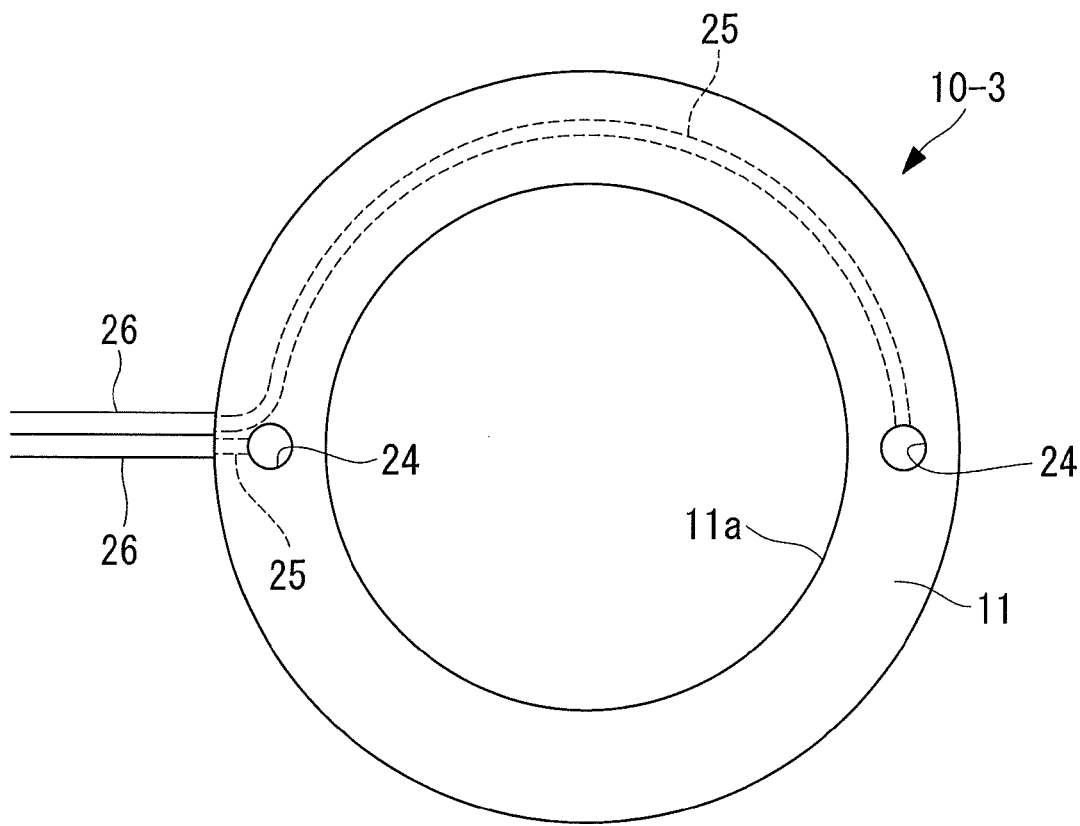
FIG. 31 is a bottom view illustrating a modification of the space ensuring device in FIG. 8.
Figure 32:
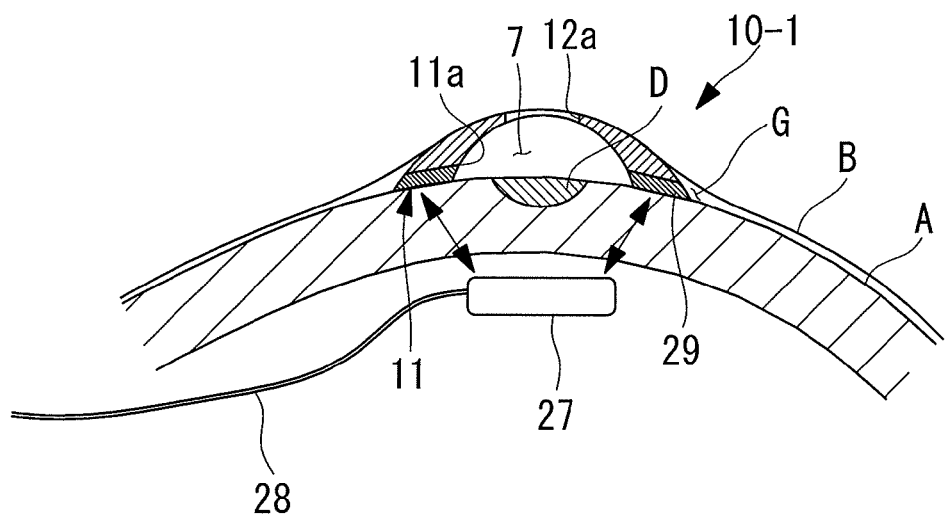
FIG. 32 is a longitudinal sectional view illustrating how a modification of the space ensuring device in FIG. 6 is used in the pericardial space.

Alternatively, as shown in FIGS. 31 and 32, space ensuring devices (the space ensuring devices 10-3 and 10-1 are used as examples here) having attaching means for attaching the heart pressing part 11 on the surface of the heart A may be adopted.

In an example shown in FIG. 31, as the attaching means, a space ensuring device 10-3 having an attachment hole 24 on the face of the heart pressing part 11 that comes into tight contact with the surface of the heart A is provided. The attachment hole 24 is connected to a communicating hole 25 and a tube 26 for supplying a negative pressure. By supplying a negative pressure via the communicating hole 25 and the tube 26, it is possible to securely attach the heart pressing part 11 on the surface of the heart A via the attachment hole 24. By securely attaching the heart pressing part 11 at a desired position surrounding the treated area D, it is possible to perform observation and the procedure stably.

On the other hand, in an example shown in FIG. 32 a probe 28 having a magnet 27 at its distal end is placed inside the heart A, and a magnetic material 29 is provided at the heart pressing part 11 of the space ensuring device 10-1. Thus, it is possible to securely attach the heart pressing part 11 on the surface of the heart A by a magnetic attracting force that occurs between the magnet 27 and the magnetic material 29. Instead of the magnetic material 29 provided at the heart pressing part 11, a magnet may be provided. In this case, either a magnet or a magnetic material is provided at the distal end of the probe 28.

Alternatively, a bioadhesive may be used to immobilize the heart pressing part 11 on the surface of the heart A. Alternatively, a space ensuring device may be immobilized on the pericardium B instead of the surface of the heart A. As the immobilizing method, a magnet (not shown) that generates a magnetic repelling force in conjunction with the magnet 27 placed inside the heart A may be provided at the heart pressing part 11, or other arbitrary immobilizing methods may be used, such as bonding with an adhesive, suction with a negative pressure, gripping, or puncturing.

From the embodiments described above, the following aspects of invention are derived.

A first aspect of the present invention is a space ensuring device comprising: a pericardium pressing part for pressing a pericardium from the pericardial space side; a heart pressing part for pressing the surface of a heart from the pericardial space side; and an interconnecting part interconnecting the pericardium pressing part and the heart pressing part, wherein the interconnecting part generates the resilient force enabling expansion against a pressure applied by a pericardium and a heart so as to ensure a space between the pericardium pressing part and the heart pressing part.

According to the first aspect, the pericardium pressing part and the heart pressing part are pushed by the resilient force of the interconnecting part in directions moving away from each other, whereby the space ensuring device expands. As a result, the pericardium is moved away from the surface of the heart, so that a space is formed between the pericardium pressing part and the heart pressing part. Accordingly, by introducing an endoscope, a surgical instrument, or the like from outside into the space, it becomes possible to operate the endoscope or surgical instrument without interference by the pericardium or the heart.

In the above first aspect, the pericardium pressing part may be formed in a plate shape, and a reflecting surface that reflects illuminating light may be provided on a face of the pericardium pressing part opposite the side that comes into contact with the pericardium.

With this configuration, with the space ensuring device expanded between the heart and the pericardium, by radiating illuminating light toward the pericardium pressing part from the distal end of an endoscope or the like introduced into the space, the illuminating light is reflected by the reflecting surface provided on the pericardium pressing part, and the reflected light irradiates the surface of the heart facing the reflecting surface. Accordingly, it is possible to ensure a distance from the illuminating-light radiating end to the surface of the heart, so that it becomes possible to illuminate a wide area of the surface of the heart without using excessively spread light.

In the above first aspect, the pericardium pressing part may have a pericardium-side opening through which the space is opened to the pericardium side, the heart pressing part may have a heart-side opening through which the space is opened to the heart side, and the interconnecting part may be formed in a ring shape that becomes progressively wider from the pericardium pressing part toward the heart pressing part.

With this configuration, when pushed out into the pericardial space, the space ensuring device expands so as to widen the gap between the pericardium and the heart with the pericardium pressing part coming into contact with the pericardium and the heart pressing part coming into contact with the heart, thereby forming a space inside thereof. The space is opened to the pericardium side through the pericardium-side opening and is opened to the heart side through the heart-side opening. With the interconnecting part formed in the ring shape becoming progressively wider from the pericardium pressing part toward the heart pressing part, it is possible to readily move an endoscope or the like inserted into the pericardial space so as to advance following the outer surface of the interconnecting part and to readily introduce the distal end of the endoscope or the like into the space from between the pericardium pressing part and the pericardium via the pericardium-side opening. Accordingly, it is possible to observe the surface of the heart with the distal end of the endoscope or the like placed at a position remote from the surface of the heart.

In the configuration in which the interconnecting part is formed in the ring shape, the interconnecting part may have an outer surface formed of an outward convex curved surface at least in the vicinity of the pericardium pressing part.

With this configuration, it is possible to readily introduce an endoscope or the like following the outer surface of the interconnecting part through the pericardium-side opening of the pericardium pressing part.

Alternatively, in the configuration in which the interconnecting part is formed in the ring shape, the interconnecting part may have an outer surface formed of an outward concave curved surface at least in the vicinity of the heart pressing part.

With this configuration, it is possible to gradually increase the inclination angle from the surface of the heart to the outer surface of the interconnecting part. Accordingly, an endoscope or the like introduced following the surface of the heart in the pericardial space can be advanced more easily onto the outer surface of the interconnecting part.

In the configuration with the outer surface formed of the convex or concave curved surface, one or more grooves extending from an outer edge of the heart pressing part to an inner edge of the pericardium-side opening may be provided on the outer surface.

With this configuration, it is possible to readily guide an endoscope or the like advanced onto the outer surface of the interconnecting part to the pericardium-side opening following the grooves.

In the above configuration, the heart pressing part may be formed in a substantially U shape surrounding a part of the space, and the interconnecting part may have an opening communicating between the interior and exterior of the space.

With this configuration, it is possible to place the space ensuring device so that the U-shaped heart pressing part surrounds a region to be treated on the surface of the heart. Thus, by introducing an endoscope or the like into the space via the opening provided on the interconnecting part, it becomes possible to operate the endoscope or the like without interference by the heart, the pericardium, or the like.

In the above configuration, the interconnecting part may have an opening communicating between the interior and exterior of the space, and the heart pressing part, at least on a part thereof, may have an inclined surface that becomes higher from the outside toward the inside of the opening.

With this configuration, when an endoscope or the like is introduced into the space, it is possible to float the distal end thereof above the surface of the heart with the inclined surface. Accordingly, it becomes possible to perform observation or a procedure at a position remote from the surface of the heart.

In the above configuration, the space ensuring device may have a plurality of division lines for dividing the space ensuring device into a plurality of segments.

With this configuration, after completing observation or the procedure, when withdrawing the expanded space ensuring device, it is possible to readily divide the space ensuring device into a plurality of segments at the division lines, which facilitates the withdrawing task.

Furthermore, in the above invention, the space ensuring device may be formed of a biocompatible plastic or metallic material.

In the first aspect, the space ensuring device may include attaching means for attaching the heart pressing part to the surface of the heart.

With this configuration, it is possible to securely attach the space ensuring device to the surface of the heart by using the attaching means. Accordingly, even if an endoscope or the like collides with the space ensuring device during its operation, it is possible to prevent the space ensuring device from being displaced from a desired position.

In the above configuration, the attaching means may attach the heart pressing part to the surface of the heart by using a negative pressure.

Alternatively, in the above configuration, the attaching means may include a magnet that is provided at a location either inside the heart or at the heart pressing part and a magnet or magnetic material provided at the other location.

With these configurations, it is possible to readily and securely attach the space ensuring device to the surface of the heart.

In the first aspect, a space ensuring device may be deformable between a contracted state in which the space ensuring device can be accommodated inside a guide tube that is inserted into a pericardial space and an expanded state in which the space ensuring device is released out of the guide tube and is thereby expanded.

With this configuration, when the guide tube (sheath, endoscope, or the like) is inserted into the pericardial space and the space ensuring device accommodated inside the guide tube in the contracted state is pushed out of the guide tube, the space ensuring device released from the guide tube is caused to return to the expanded state by its resilient force, whereby the space ensuring device expands in the pericardial space. Thus, the pericardial space is dilated to a predetermined size only, and unnecessary dilation is prevented. The space is opened to the surface of the heart and can be entered from outside. Accordingly, by introducing the distal end of an endoscope or a surgical instrument from outside into the formed space, maneuverability can be improved while preventing the pericardium or the heart from interfering with the operation of the endoscope or surgical instrument. A second aspect of the present invention is a space ensuring method comprising: inserting a space ensuring device according to claim 1 that is accommodated inside a guide tube into a pericardial space; and releasing the space ensuring device out of the guide tube to expand so as to ensure a space between a heart and a pericardium.

According to the first and second aspects of present invention, in a pericardioscopic procedure, an advantage is afforded in that, without providing an endoscope or surgical instrument with special space ensuring means and without unnecessarily dilating the pericardial space, a space necessary for operation of the endoscope or surgical instrument is ensured, so that maneuverability can be improved while suppressing complications, such as cardiac tamponade.

What is claimed is:

1. A space ensuring device for a pericardial space between a pericardium and a heart, the space ensuring device comprising:
    a pericardium pressing part for pressing the pericardium from the pericardial space side;
    a heart pressing part for pressing a surface of the heart from the pericardial space side; and
    an interconnecting part interconnecting the pericardium pressing part and the heart pressing part,
    wherein the interconnecting part is configured to generate a resilient force enabling expansion of the interconnecting part against a pressure applied by the pericardium and the heart so as to ensure a space between the pericardium pressing part and the heart pressing part,
    wherein the interconnecting part comprises an interior surface facing the space, an exterior surface substantially opposite the interior surface, a first opening communicating the interior surface and the exterior surface, and a second opening communicating the interior surface and the exterior surface,
    wherein from the exterior surface toward the interior surface, the first opening is inclined in a direction away from the heart pressing part such that a first instrument inserted through the first opening from the exterior surface toward the interior surface is oriented away from the heart pressing part, and
    wherein from the exterior surface toward the interior surface, the second opening is inclined in a direction away from the pericardium pressing part such that a second instrument inserted through the second opening from the exterior surface toward the interior surface is oriented away from the pericardium pressing part.

2. The space ensuring device according to claim 1, wherein the pericardium pressing part is formed in a plate shape comprising:
    a first face that comes into contact with the pericardium; and
    a second face, substantially opposite the first face, having a reflecting surface that reflects illuminating light.

3. The space ensuring device according to claim 1, wherein the heart pressing part is formed in a substantially U shape surrounding a part of the space.

4. The space ensuring device according to claim 1, wherein one or more of the pericardium pressing part, the heart pressing part and the interconnecting part is formed of a biocompatible plastic material.

5. The space ensuring device according to claim 1, wherein the interconnecting part is deformable between:
    a contracted state in which the space ensuring device is accommodated inside a guide tube that is inserted into the pericardial space against the resilient force generated by the interconnecting part, and
    an expanded state in which the space ensuring device is released out of the guide tube and is thereby expanded by the resilient force generated by the interconnecting part to ensure the space between the pericardium pressing part and the heart pressing part.

6. The space ensuring device according to claim 1,
wherein the pericardium pressing part is provided on a first plane,
wherein the heart pressing part is provided on a second plane substantially parallel to the first plane,
wherein the interconnecting part expands in a direction that is substantially orthogonal to the first plane and the second plane to ensure the space between the pericardium pressing part and the heart pressing part.

* * * * *